United States Patent
Kost et al.

(10) Patent No.: US 8,670,991 B2
(45) Date of Patent: Mar. 11, 2014

(54) AUTHENTICATING PRESCRIBER IDENTITY TO ENABLE ELECTRONICALLY ORDERING DRUG SAMPLES FROM A DRUG SAMPLE FULFILLMENT PLATFORM

(76) Inventors: Cecil Kost, Chapel Hill, NC (US); Timothy Chrobuck, Seattle, WA (US); David V. Tovrea, Lake Stevens, WA (US); Scott M. King, Issaquah, WA (US); Mark D. Gleason, Oak Park, IL (US)

( * ) Notice: Subject to any disclaimer, the term of this patent is extended or adjusted under 35 U.S.C. 154(b) by 2540 days.

(21) Appl. No.: 11/107,399

(22) Filed: Apr. 14, 2005

(65) Prior Publication Data

US 2006/0161453 A1 Jul. 20, 2006

Related U.S. Application Data

(63) Continuation-in-part of application No. 10/674,904, filed on Sep. 30, 2003.

(60) Provisional application No. 60/472,956, filed on May 22, 2003.

(51) Int. Cl.
G06Q 50/24 (2012.01)
(52) U.S. Cl.
USPC .................................... 705/2; 705/3
(58) Field of Classification Search
USPC ............................................................ 705/2
See application file for complete search history.

(56) References Cited

U.S. PATENT DOCUMENTS

| | | | | |
|---|---|---|---|---|
| 6,564,121 | B1 * | 5/2003 | Wallace et al. | 700/231 |
| 6,670,885 | B2 * | 12/2003 | Kosaka | 340/309.16 |
| 6,687,390 | B2 * | 2/2004 | Avni et al. | 382/119 |
| 6,687,676 | B1 * | 2/2004 | Denny | 705/2 |
| 6,702,146 | B2 * | 3/2004 | Varis | 221/3 |
| 6,952,681 | B2 * | 10/2005 | McQuade et al. | 705/28 |
| 6,996,216 | B2 * | 2/2006 | Brown et al. | 379/114.01 |
| 2002/0032582 | A1 | 3/2002 | Feeney, Jr. et al. | |
| 2005/0125257 | A1 * | 6/2005 | Ziegele et al. | 705/3 |

OTHER PUBLICATIONS

SamplesMD, Business Plan.
SamplesMD, Presentation Slides.
SamplesMD, SamplesMD Application.
SamplesMD, "A Partner for Growth with the Pharmaceutical Industry."

* cited by examiner

*Primary Examiner* — Valerie Lubin
*Assistant Examiner* — Reginald R Reyes
(74) *Attorney, Agent, or Firm* — John H. Pearson, Jr., Esq.; Walter F. Dawson, Esq.; Pearson & Pearson, LLP

(57) ABSTRACT

A fully online process to facilitate the fulfillment of drug samples to prescribers is described. With the present invention, a prescriber may order physical drug samples online by undergoing an authentication process that is in lieu of requiring a signature match. In the invention, the ordering of drug samples is made over a communication network without requiring a handwritten signature.

22 Claims, 23 Drawing Sheets

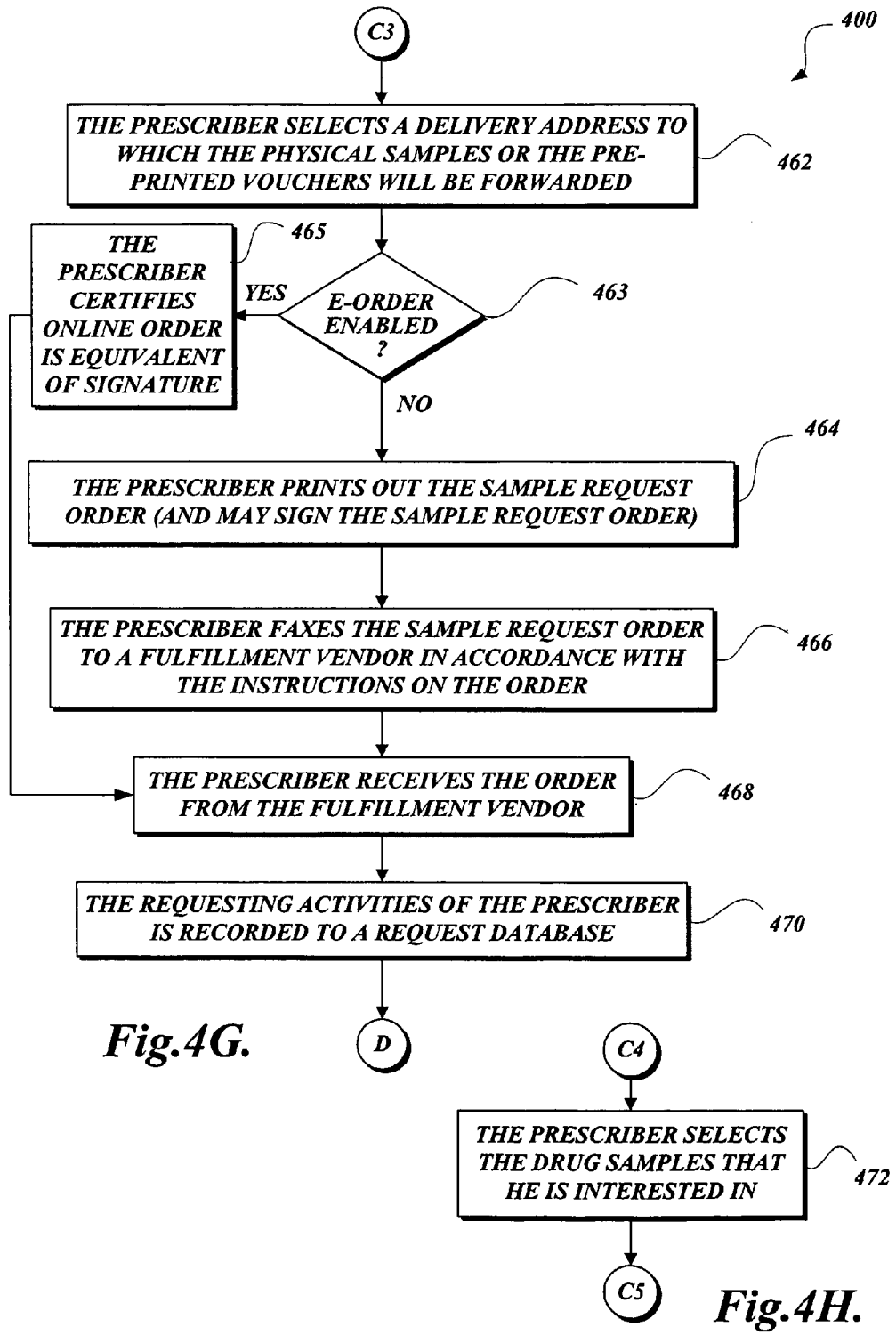

AUTHENTICATING PRESCRIBER IDENTITY TO ENABLE ELECTRONICALLY ORDERING DRUG SAMPLES FROM A DRUG SAMPLE FULFILLMENT PLATFORM

CROSS-REFERENCE TO A RELATED APPLICATION

This application is a continuation in part of U.S. patent application Ser. No. 10/674,904, filed Sep. 30, 2003, which claims the benefit of U.S. Provisional Application No. 60/472,956, filed May 22, 2003, both applications are expressly incorporated herein by reference.

FIELD OF THE INVENTION

The present invention is related to a method and system for authenticating a prescriber to enable the ordering of drug samples over a communication network.

BACKGROUND OF THE INVENTION

From idea to production, the development of a new drug can take up to 10 years and cost about $800 million. But many risks abound in the development process that can cause complete failure. The process usually starts with the idea that an existing chemical substance has therapeutic value or that the structure of an existing drug can be modified for new clinical uses. Out of 10,000 chemicals tested in a laboratory, only one may eventually become a drug. Besides the expense necessary to produce them, drugs are heavily regulated by the bureaucracy of government agencies. In the United States, the FDA not only approves new drugs, but also determines how drugs are produced and sold by continually monitoring the development and use of all drugs sold. This is the backdrop against which a pharmaceutical company ("pharma 102") markets its precious few developed drugs 104. See FIG. 1.

Traditionally, a sales representative 106 of the pharma 102 visits one or more prescribers 110, leaves behind some drug samples of the drugs 104, and waits in trust that the prescribers 110 will prescribe these drug samples to their patients. When a sales representative 106 visits a prescriber, such as one of the prescribers 110, the sales representative 106 is performing two actions together called a drug detail. First, the sales representative 106 educates the prescriber about the efficacy of the drug samples for various disease states and differentiates them from any competitive drugs in the marketplace. Second, the sales representative 106 leaves drug samples behind with the prescriber so that he can dispense these drug samples to his patients.

A triangle 108 hierarchically organizes all prescribers into deciles, which are numbers that divide a frequency distribution (the regularity of which a prescriber prescribes drugs) into 10 classes such that each contains the same number of prescribers. The upper 1-3 deciles describe one or more prescribers 110. The remaining 4-10 deciles describe one or more prescribers 112. Prescribers at deciles 1-3 comprise 25 percent of all prescribers and generate 50 percent of all prescriptions. The remaining 75 percent of prescribers are at deciles 4-10 and prescribe the remaining 50 percent of all other prescriptions. Because individual prescribers at deciles 4-10 do not generate as much income for the pharma 102 compared to those in the top three deciles, the sales representative 106 typically does not visit these prescribers, but instead, focuses her efforts on prescribers 110 at deciles 1-3.

The reason for this is mainly economic. For each sales representative 106, the pharma 102 incurs numerous expenses including purchasing and maintaining an automobile for the sales representative 106 to travel to the prescribers, and paying a salary, benefits, and so on. Also a growing number of billions of dollars are spent each year on everything necessary to support the distribution of drug samples, such as packaging and delivery. When this cost is multiplied by the cost of employing multiple sales representatives, the pharma 102 cannot afford to visit all prescribers to solicit patronage of its drugs.

But there are still other reasons beyond the economic ones that prevent the sales representative 106 from visiting all prescribers. One or more prescribers 112 may be located in remote areas making it difficult for the sales representative 106 to reach them. Certain prescribers 112 do not wish to see a sales representative 106 because they are too busy with their practice or they belong to an organization, such as a hospital, that forbids sales representatives from soliciting prescribers on its premises. Another reason why most prescribers 112 are not visited by the sales representative 106 has to do with absences by the sales representative 106 because of parental leaves, military duties, firings, layoffs, or unexpected resignations, and so on.

While it is cost prohibitive for the pharma 102 to send sales representatives to visit all prescribers, prescribers who know about the drug samples and want access to drug samples have problems too. If the prescriber were to be interested in designing a therapy from five different brands of drugs, he might have to track down five different sales representatives to get the drug samples. The prescriber's preferences are completely ignored. The biggest dissatisfaction of all among prescribers, however, is the lack or inconsistent supply of physical samples in their hands. These prescribers may not have easy access to the sales representative 106. And even if access were possible, the sales representative 106 may not have a ready supply of physical samples for these prescribers to use. The literature has shown that if a prescriber is dissatisfied with a drug brand due to lack of physical samples, the prescriber will not prescribe that particular drug brand to patients.

When the sales representative 106 leaves drug samples with the prescriber, the prescriber signs an acknowledgment indicating that these drug samples are now in his possession. Beyond that, however, there is no data that tracks whether drug samples actually get prescribed to patients of the prescriber. No additional information is possible beyond the point at which drug samples are given to the prescriber. So even though the pharma 102 has spent a great deal of money on drug samples, it has no means of knowing whether the physical samples were actually prescribed to patients or tossed uselessly into a garbage can. Without a way to track these drug samples, the pharma 102 cannot improve its drug sample distribution. Moreover, without tracking, expired drug samples may be prescribed to patients, diminishing their efficacy. This may add to wrongful impressions by patients regarding the drug's effectiveness and eventually will lead to a lack of acceptance of the drug in the marketplace.

In the commonly assigned application Ser. No. 10/674,904, a drug sample fulfillment platform is disclosed that may be used by prescribers of drugs for the ordering of drug samples. This prior application describes that to place a drug sample order, a prescriber is required to print the order, sign the order, and then fax the order to the drug sample fulfillment vendor. If the order contains drugs from two vendors, then two faxes need to be sent. This process is burdensome on the prescribers, but necessary to ensure that only true prescribers may use the system. Normally, the responsibility of determining whether the prescriber whose name is on the order form is, in fact, the prescriber who is requesting the drug samples, falls on the drug sample fulfillment vendor.

The Prescription Drug Marketing Act (PDMA) and the Code of Federal Regulations, both of the United States, place requirements on drug sample fulfillment vendors to verify the identity of the prescriber and the validity of the shipping address prior to sending the drug samples. This is typically done by maintaining a copy of the prescriber's signature and a file containing address information about the prescriber. Upon receipt of the request for drug samples, i.e., the faxed form containing the prescriber's signature, the information on the request is validated by the fulfillment vendor against the file copy. Assuming the information matches, the fulfillment vendor fills the order and ships the drug samples to the prescriber. In addition, the fulfillment vendor will require verification that the drug sample order was received. One example of verification may be to require the prescriber to sign and return a card that may be included within the package. The card must be signed by the prescriber and returned to the fulfillment vendor as a positive indication that the shipment has been received. If the prescriber refuses to sign and return the card, or the card is otherwise not returned, the fulfillment vendor will generally refuse further orders from that particular prescriber until the reply card is received. Another verification method that the fulfillment vendor may utilize is to refer to the signed receipt from the package carrier that is signed by the package recipient.

As more and more prescribers begin to use communication networks, such as the global TCP/IP network, commonly referred to as the Internet, for continuing medical education, ordering medical supplies, and so on, there is also an increasing demand to enable the ordering of physical drug samples over a communication network to reduce the time between the placement of the order and the receipt of the drug samples. However, the current method of authenticating prescribers is inadequate and stands in the way of fully conducting drug sample ordering over the Internet. To make the process fully online would require a mechanism to identify valid prescribers who can issue valid orders to fulfillment vendors. The process, however, does not remove the obligation of the fulfillment vendor to perform its normal validity checks, since the PDMA requirements will continue.

Accordingly, there is an increasing need to provide a method and system for the online, real-time, authentication of a prescriber, to provide for a more expedient manner of delivering drug samples from the fulfillment vendors to the prescribers. This will not only benefit the prescribers, but will also benefit the pharmaceutical companies because the more of their drug samples that are prescribed, the more readily accepted the drugs will become in the marketplace.

In sum, not only is it expensive and laborious to develop new drugs, but the traditional drug sample distribution process does not allow the pharma 102 to assess the effectiveness of its drug sample fulfillment program further increasing financial risk to the pharma 102. Not all prescribers can be reached by the sales representative 106, hence limiting the distribution of drug samples to patients who may benefit from them. On the other hand, prescribers who do wish to have an opportunity to try the drug samples cannot readily obtain a consistent supply. Thus, there is a need for an architecture for enhancing drug sample fulfillment distribution while avoiding or reducing the foregoing and other problems.

SUMMARY OF THE INVENTION

In accordance with this invention, a system and method for enhancing drug sample fulfillment distribution, is provided.

One aspect of the invention is the online and real-time authentication of prescribers. Online authentication, in accordance with the invention, generally requires the user to provide authentication descriptors that the prescriber and trustworthy entities, such as government regulatory bodies, would know. An authentication descriptor is information pertaining to a prescriber used in authenticating the identity of the person. Accuracy of the authentication may be improved by requiring additional authentication descriptors to be validated and by increasing the number of sources from which those authentication descriptors are drawn. Additionally, the strength of the authentication descriptor to positively identify a prescriber may also be factored in by assigning "weighted" values to some authentication descriptors. For example, asking for a phone number requires only that an imposter have a phone book; asking for a phone number and a credit card requires the imposter to have both a phone book and a credit report, which is much more difficult to obtain.

In the context of authenticating prescribers, data on the prescribers may be obtained by the American Medical Association (AMA) and state licensing boards. The data on prescribers is already being aggregated by commercial companies offering Physician Verification Services (PVS), albeit, for a completely different use as described herein. These services typically operate by accepting as input a set of identifying data (such as a name and address), using various matching algorithms to identify the associated prescriber information, and returning the input information augmented by the additional AMA/state medical board information. Presently, the PVS are not being used for the authentication of a prescriber over a communication network for the purpose of enabling a transaction involving medications.

One aspect of the invention is related to a method for the authentication of a prescriber over a communication network to enable a transaction involving a medication, or prescription drug, such as the ordering of physical drug samples. The method may be executed on various computer systems being communicatively connect over a communication network, such as the Internet. To authenticate a prescriber, the method obtains, from the prescriber, authentication descriptors including: first name, last name, DEA number, state medical license number, state of licensure, professional designation, medical school attended, year of medical school graduation, and date of birth. The information is communicated over a communication network, and a Web service using the databases of the PVS, may return a global "Yes" or "No" as to the accuracy of all the information as a whole, or return a "Yes" or "No" as to the accuracy of each authentication descriptor, or fill in any missing fields of information. If there is one or more authentication descriptors that do not match, the prescriber may be given numerous attempts to correct any information. When a specified set of authentication descriptors match, the prescriber is authenticated and may carry out transactions involving medications. However, if the prescriber exceeds the number of permitted attempts at correcting erroneous information, the prescriber may be directed to contact a customer representative. The method may further include requiring a prescriber that has been authenticated to provide a strong password and User ID to be used to open an online ordering account. As a condition for opening an ordering account, the prescriber may be asked to certify that the User ID and password used for orders sent electronically over a communication network are the equivalent of, and have the legal effect of, a handwritten signature. In other words, the User ID and password are the electronic signature of the prescriber. Additionally, the prescriber may be asked to maintain the User ID and password confidential. To memorialize this understanding, and to complete the registration process, the prescriber may be asked to print, sign and return a form or a statement to such effect. The method may also include sending a document to the address provided by the PVS, notifying the prescriber of the successful registration for electronic ordering and requesting immediate notification if the prescriber has not requested such registration. Additionally, the document may once again request the prescriber to maintain the User ID and password confidential to prevent fraudulent use. This step is to prevent fraudulent accounts. The prescriber may be asked to perform the registration process for electronic ordering once, or alternatively, the prescriber may be authenticated and asked to register periodically to maintain the system with current prescribers.

In accordance with another aspect of the invention, a method that may be executed in a networked system of one or more computers, is provided for authenticating a prescriber over a communication network for placing an order for a medication over the communication network. The method includes obtaining, from a prescriber, authentication descriptors that are characteristic of the prescriber. The method includes verifying that the authentication descriptors match with prescriber information from a provider of prescriber information. When a selected set of authentication descriptors matches, the prescriber may be enabled to order medications over the communication network.

In accordance with another aspect of the invention, a system for distributing pharmaceutical drugs, is provided. The system includes a drug sample fulfillment platform for accessing drug sample services and a set of Web pages coupled to the drug sample fulfillment platform through which a prescriber may be authenticated over a communication network for ordering drug samples over a communication network.

In accordance with another aspect of the invention, a networked system for authenticating the identity of a prescriber of pharmaceutical drugs, is provided. In this aspect of the invention, the system includes a drug sample fulfillment platform that comprises a drug sample Web site for mating with a Web portal when a prescriber selects a hyperlink, the drug sample Web site presenting one or more Web pages for authenticating the identity of a prescriber of pharmaceutical drugs, wherein the drug sample fulfillment platform is communicatively coupled via a communication network to a provider of prescriber information.

In accordance with another aspect of the invention, a drug sample fulfillment platform, is provided. The drug sample fulfillment platform includes a drug sample Web site for mating with a portal. The drug sample fulfillment platform includes a request database for receiving requests of a prescriber through the drug sample Web site for drug samples. The request database may respond to the prescriber by allowing the prescriber to place an order for drug samples and electronically transmitting a drug sample request order to a drug sample fulfillment vendor over a communication network.

In accordance with another aspect of the invention, a drug sample ordering system, is provided. The drug sample ordering system includes a drug sample fulfillment platform comprising a prescriber authentication engine for authenticating the identity of a prescriber by comparing a plurality of authentication descriptors characteristic of the prescriber against prescriber information from an information provider of prescriber information and obtaining a confirmation for each of the authentication descriptors that matches with the information provider's information. When the prescriber is authenticated, the prescriber may order drug samples via the drug sample fulfillment platform.

In accordance with another aspect of the invention, a networked system that executes a method for processing an order for a drug sample received over a communication network, is provided. The method includes, obtaining, over the communication network, a drug sample request order, wherein the drug sample request order is from a prescriber that may be authenticated by comparing prescriber provided information against prescriber information obtained from a provider of prescriber information, and processing the drug sample request order.

In accordance with another aspect of the invention, a networked system for authenticating a prescriber in real time, over a communication network, is provided. The system includes a plurality of entities each having a computer or computer system, each computer or computer system being communicatively connected via a communication network, such as the Internet, to enable each of the entities to communicate with, and send or receive information over the communication network to and from, one or more, other entities. The entities in the system include a prescriber, a provider of a drug sample fulfillment platform, an information provider of prescriber information, and a drug sample fulfillment vendor. The drug sample fulfillment platform may include a drug sample Web site for mating with a Web portal when a prescriber selects a hyperlink. The drug sample Web site presents one or more Web pages for authenticating the prescriber and opening a drug sample ordering account for the prescriber to order drug samples over the communication network. The drug sample fulfillment platform is able to communicate with the information provider and compare a prescriber profile containing authentication descriptors regarding the prescriber with information provided by the information provider, which the information provider is able to either verify is correct or identify as incorrect. The drug sample fulfillment platform may further generate Web pages for the prescriber to place an order for drug samples, and the drug sample fulfillment platform is able to electronically send the order to the drug sample fulfillment vendor who fills the order and ships the order to the prescriber.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 4A-4M are process diagrams illustrating a method for enhancing a drug sample fulfillment program, according to one embodiment of the present invention;

DETAILED DESCRIPTION OF THE PREFERRED EMBODIMENT

Figure 1:
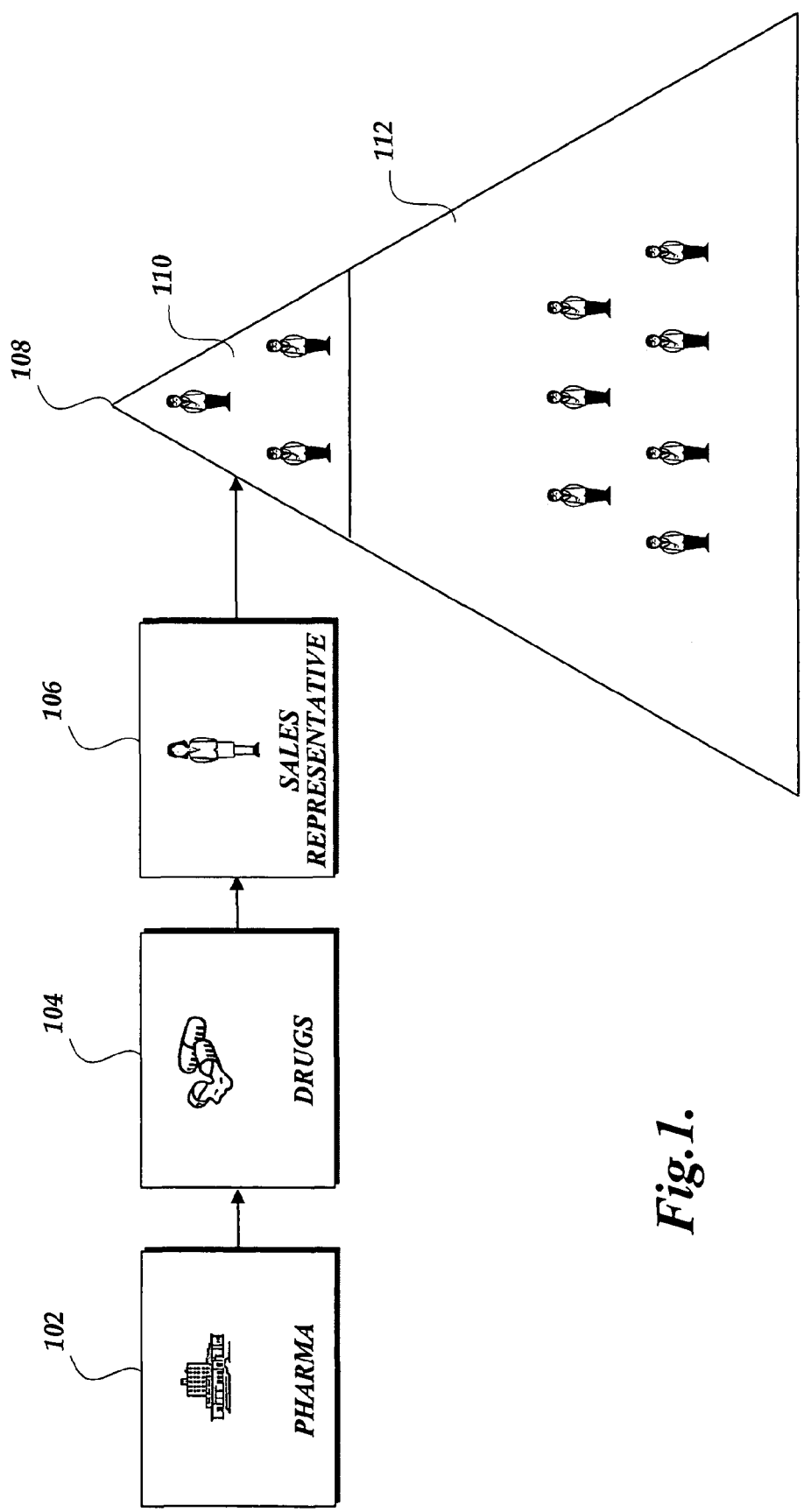
FIG. 1 is a block diagram illustrating a conventional system showing various problems of distributing drug samples to prescribers.

A system in which drug samples 212 are distributed to one or more prescribers 210 without the need to employ sales representatives is illustrated. A pharma 202 is a company engaged in the manufacture and sale of pharmaceuticals, which are medicinal drugs used for therapeutic applications. The term "prescribers" as referred to herein includes, but is not limited to, physicians; physician assistants; certified registered nurse practitioners; advanced registered nurse practitioners; and other licensed professionals authorized to prescribe medications.

Throughout a series of stages through which a drug passes during its lifetime, starting with its launch, continuing with its maturation in the marketplace, and concluding with the end of its patent life cycle, a brand manager 204 is assigned by the pharma 202 to manage the drug sample distribution to prescribers 210. The brand manager 204 begins a drug sample distribution program by first identifying a group of prescribers 210. The brand manager 204 selects these prescribers 210 by excluding or including each prescriber based on criteria defined by the brand manager 204 (e.g., medical practice specialty, therapeutic class to which drug samples belong, prescribing volume and behavior). Prescribers 210 can also be selected via their Drug Enforcement Agency (DEA) number or individually by the brand manager 204. The DEA number is a unique global identifier that identifies a particular prescriber who prescribes drugs in the United States.

After the brand manager 204 has selected a group of prescribers 210, the brand manager 204 produces a set of brand rules 206 which define the availability of drug samples to each of the prescribers 210. The set of brand rules 206 may cause one prescriber's drug sample availability and characteristics to be different from those of another prescriber. Thus, for each prescriber there is a virtual drug sample cabinet tailored specifically for that prescriber. Preferably, the group of prescribers 210 is divided into segments. The brand rules provide personalization and customization for each segment. Many other personalization capabilities to tailor the distribution of drug samples to prescribers 210 are possible, such as various delivery methods; various drug strengths; trademark and local presentation of drug samples; customized drug disclaimers; specific product, package, and brand Web sites; and facilitating the scheduling of prescriber interactions with sales representatives or medical science liaisons.

The set of brand rules 206 are used to focus the drug sample fulfillment platform 208 to distribute drug samples to prescribers 210. The drug sample fulfillment platform 208 is preferably a Web-based platform that enables registered health care professionals, pharma 202's sales representatives, and other authorized users to order drug samples and obtain related drug information via the Internet. The drug sample fulfillment platform 208 is also preferably electronically linked to one or more prescriber-oriented online portals (such as Web MD), an e-Detailing service (such as Lathian's MyDrugRep.com), or to a prescriber's practice management software running on a computer system in the prescriber's office.

The drug sample fulfillment platform 208 is tailored based on the brand rules 206 established by the brand manager 204 for each drug and prescriber segment. Using the drug sample fulfillment platform 208, the brand manager 204 can select which prescribers are authorized to use the drug sample fulfillment platform 208 and the services provided thereon, the forms of drug samples they can access, and the drug sample quantity and delivery method. The drug sample fulfillment platform 208 can be configured to allow a prescriber to request a physical sample drop shipment. Requests for such physical samples are electronically communicated (including facsimile transmission or networked system communications) to the brand manager 204's designated fulfillment vendors that pick, pack, and ship physical samples to the requesting prescriber's office. Using this method, prescribers 210 no longer need to rely on sales representatives to deliver physical samples. As an alternative to physical samples, the prescribers 210 use the drug sample fulfillment platform 208 to obtain pre-printed vouchers. These vouchers, when accompanied by a prescription, can be redeemed at a pharmacy 215 by patients 214 for free trial medication. The drug sample fulfillment platform 208 can be configured to allow prescribers 210 to request a drop shipment of pre-printed drug vouchers. If the brand rules 206 allow, prescribers 210 may print on demand coupons from the drug sample fulfillment platform 208. These online, on demand print coupons are printed real-time in the prescriber's office. The prescriber signs the printed coupon as a prescription or attaches the voucher to a prescription for the patients 214 to redeem at the pharmacy 215 to obtain free drug sample medication. One advantage of both types of vouchers is that they ensure that the drug samples distributed to patients 214 are fresh, with their efficacy not diminished by expiration.

Figure 2A:
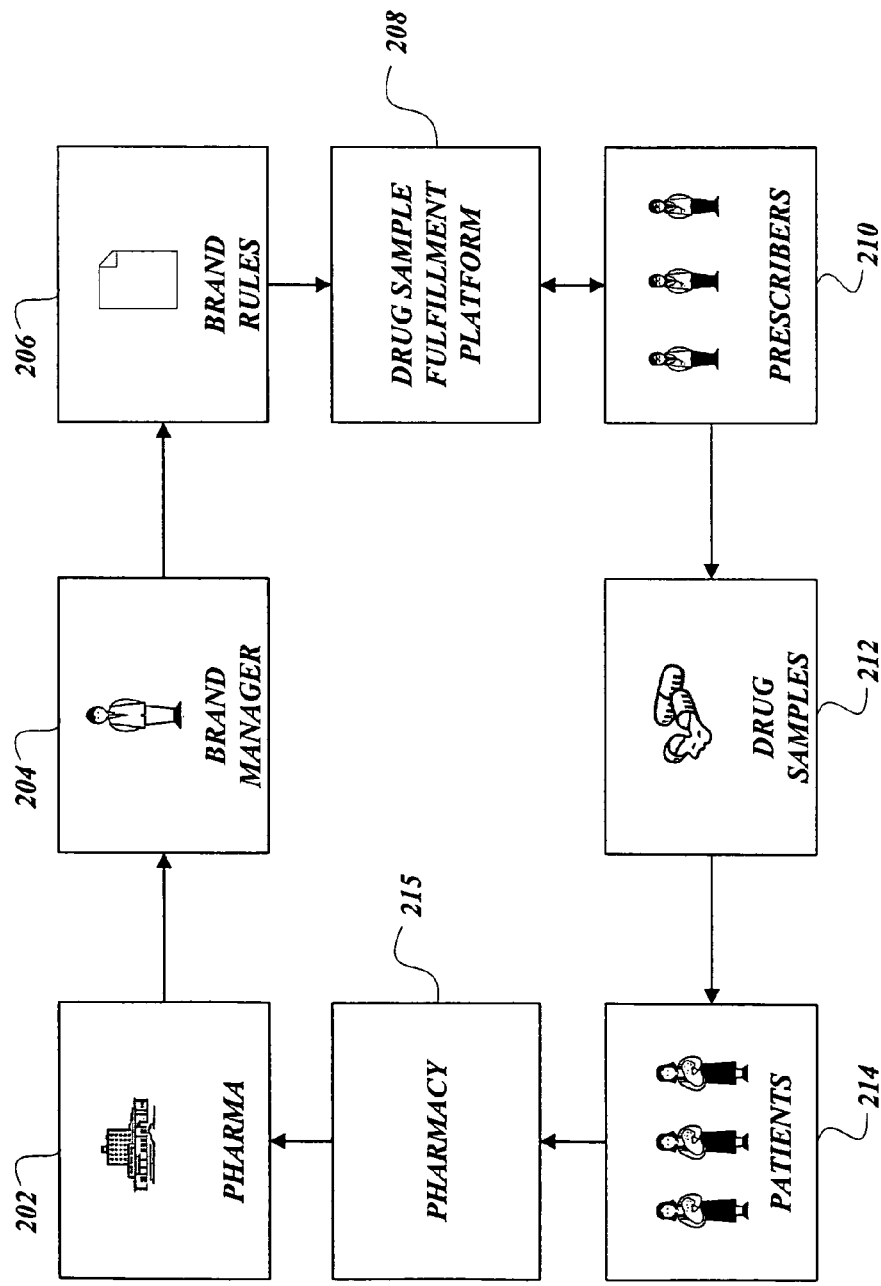
FIG. 2A is a block diagram illustrating an exemplary drug sampling fulfillment architecture.
Figure 2B:
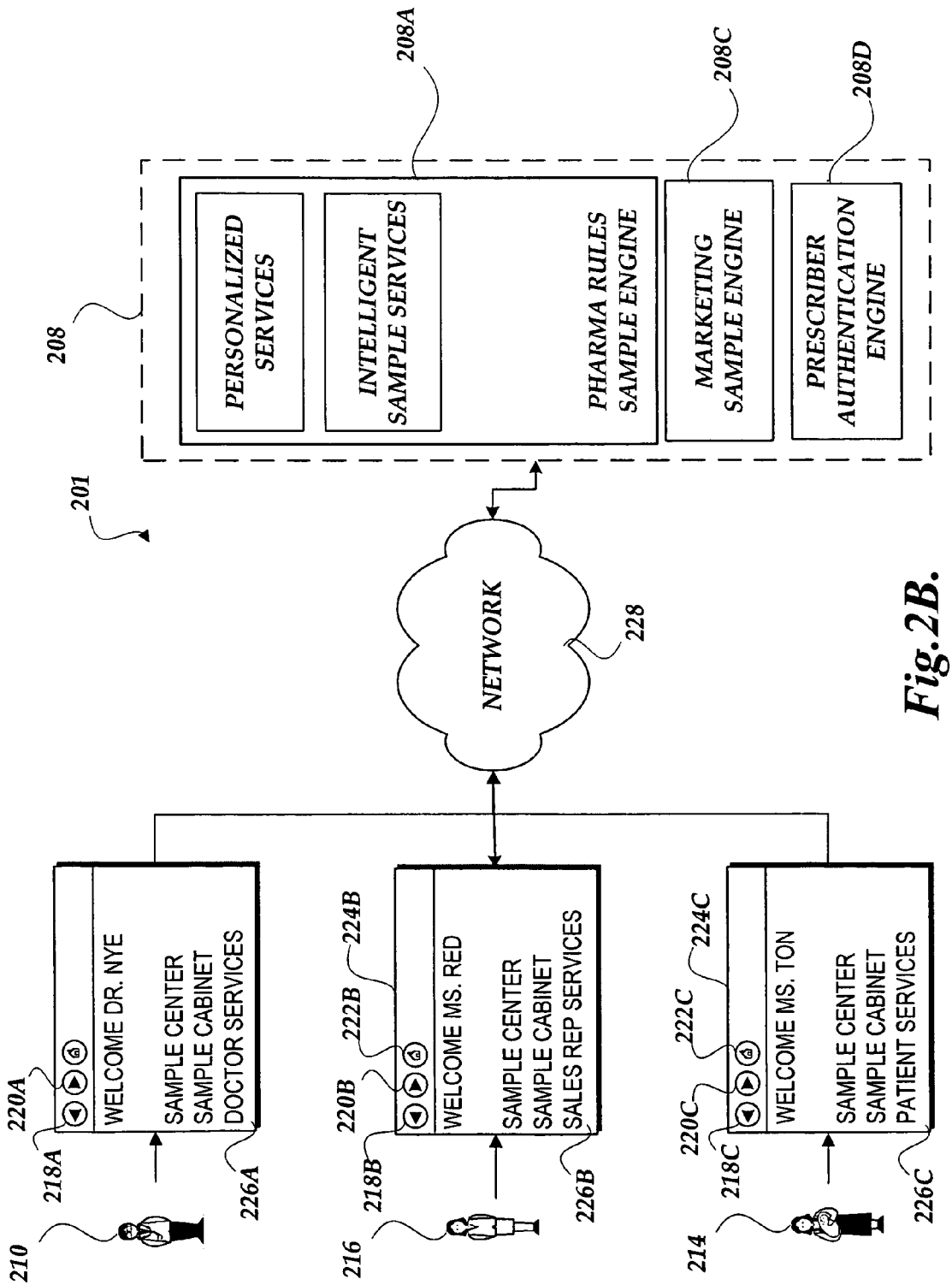
FIG. 2B is a block diagram illustrating pieces of a system for drug sample fulfillment distribution, according to one embodiment of the present invention.

FIG. 2B illustrates a system in which a prescriber 210, a sales representative 216, and a patient 214 interact with the drug sample fulfillment platform 208. This system is a networked computing environment that has pieces of hardware and software applications. The prescriber 210, the sales representative 216, and the patient 214 interact with the resources of the networked computing environment 200 via personal computers (not shown). A number of Web browsers 224A-224C run on personal computers. These Web browsers are software that let the prescriber 210, the sales representative 216, and the patient 214 view HTML documents and access files and software related to those documents on the drug sample fulfillment platform 208. Web browsers 224A-224C include a number of tools for navigation, such as BACK buttons 218A-218C and FORWARD buttons 220A-220C. These buttons are positions on navigation bars allowing easy access to Web pages by the prescriber 210, the sales representative 216, and the patient 214.

Web pages 226A-226C are each a starting point to a Web site that serves as a gateway to a collection of links, content, and services designed to guide the prescriber 210, the sales representative 216, and the patient 214 to information they are likely to find interesting that relates to drug samples and their distribution. Web pages 226A-226C include greetings that identify a particular user of the drug sample fulfillment platform 208, such as "WELCOME DR. NYE" for the prescriber 210; "WELCOME MS. RED" for the sales representative 216; and "WELCOME MS. TON" for the patient 214. Web pages 226A 226C include a hyperlink (SAMPLE CENTER), that allows access to available drug samples personalized to the particular user, and another hyperlink (SAMPLE CABINET), that allows access to the drug sample ordering history of the particular user. Hyperlinks "DOCTOR SERVICES," "SALES REP SERVICES," and "PATIENT SERVICES" of Web pages 226A 226C allow the prescriber 210, the sales representative 216, and the patient 214 to access drug information, answers to frequently asked questions, profile updates, and online drug sample information. Web pages 226A 226C and pieces of content on these Web pages are made available by the drug sample fulfillment platform 208 via a network 228. The network 228 is a group of computers and associated devices that are connected by communication facilities, such as the Internet.

The drug sample fulfillment platform 208 is one or more computers or one or more programs executing on one or more computers that respond to requests of a user, such as the prescriber 210, the sales representative 216, or the patient 214, to download Web pages 226A-226C and pieces of content associated with Web pages 226A-226C. In one embodiment, Web pages 226A-226C are preferably available as a response to an application specific messaging protocol. Web pages 226A 226B, as a response to an application specific messaging protocol, mate with a Web portal when the prescriber 210, the sales representative 216, or the patient 214 use the Web portal. The drug sample fulfillment platform 208 can push a message, such as via e-mail or a pop-up message, to the prescriber 210, when it notices that the prescriber 210 has not ordered a drug sample for a certain amount of time. Depending on the prescriber's order history, his specialty, etc., the message may be pushed to help remind the prescriber about the availability of drug samples.

In one embodiment, the drug sample fulfillment platform 208 comprises three engines, a pharma rules sample engine 208A (encompassing personalization and intelligent brand rule implementation), a marketing sample engine 208C (encompassing integration with drug sample suppliers and Web portals), and a prescriber ID authentication engine 208D (encompassing interfacing with information providers). The pharma rules sample engine 208A tailors the distribution of drug samples to one or more prescribers 210, one or more sales representatives 216, and one or more patients 214. The pharma rules sample engine 208A monitors the distribution of drug samples to a particular user, such as the prescriber 210. If the prescriber 210 does not respond to the tailored drug sample allocation as specified by the pharma rules engine 208A, the pharma rules engine 208A modifies the allocation of drug samples to the prescriber 210 so that the prescriber 210 responds more favorably, such as by prescribing to his patients the distributed drug samples. If the prescriber 210 does not respond at all, the pharma rules sample engine 208A reduces or eliminates the allocation of drug samples to the prescriber 210. The marketing sample engine 208C links or integrates the supply of drug samples and parties who are interested in drug samples, such as the prescriber 210, the sales representative 216, or the patient 214. The prescriber ID authentication engine 208D processes the prescriber supplied authentication descriptors, seeks to match the information provided by the prescriber with external databases to confirm the veracity of the information, and makes the rules as to whether a prescriber is authenticated to enable ordering drug samples online. The prescriber ID authentication engine 208D may also make the rules regarding the expiry of passwords for accessing an online drug sample ordering account. The combination of the pharma rules sample and marketing sample engines reduces or solves the problem of the lack or inconsistent supply of drug samples available for interested parties to prescribe or use. The prescriber ID authentication engine 208D obviates the need for the prescriber to manually sign and fax a drug sample request order form and for the drug sample fulfillment vendor to verify signatures.

Various embodiments of the present invention allow the sales representative 216 to access the drug sample fulfillment platform 208 to order physical samples or pre-printed vouchers to be shipped to the sales representative 216 for distribution. The sales representative 216 may have limited capacity to distribute many physical samples or massive amounts of pre-printed coupons. Instead, the sales representative 216 can access the drug sample fulfillment platform 208 to print a desired number of coupons to give to the prescriber 210. In one embodiment, to access the drug sample fulfillment platform 208, the sales representative 216 authenticates that she has the proper access by providing a territorial identifier in which she operates and her last name, among other pieces of information. Preferably, the number of coupons that the sales representative 216 can print in any one log in session is limited to a certain quantity, as specified by the brand rules 206.

The drug sample fulfillment platform 208 can also serve as an avenue for consumers, such as the patients 214, to learn about available drugs and request samples. Consumers can access the Web site and print vouchers for brand manager 204 approved drugs to take to their individual physician for signature or authorization. Thereby, consumers could be categorized as either: general consumer-individuals having public web access to a "general sample medicine cabinet"; or patient consumer-individuals with privileged access to a custom formulary program due to their health plan affiliation.

Figure 2C:
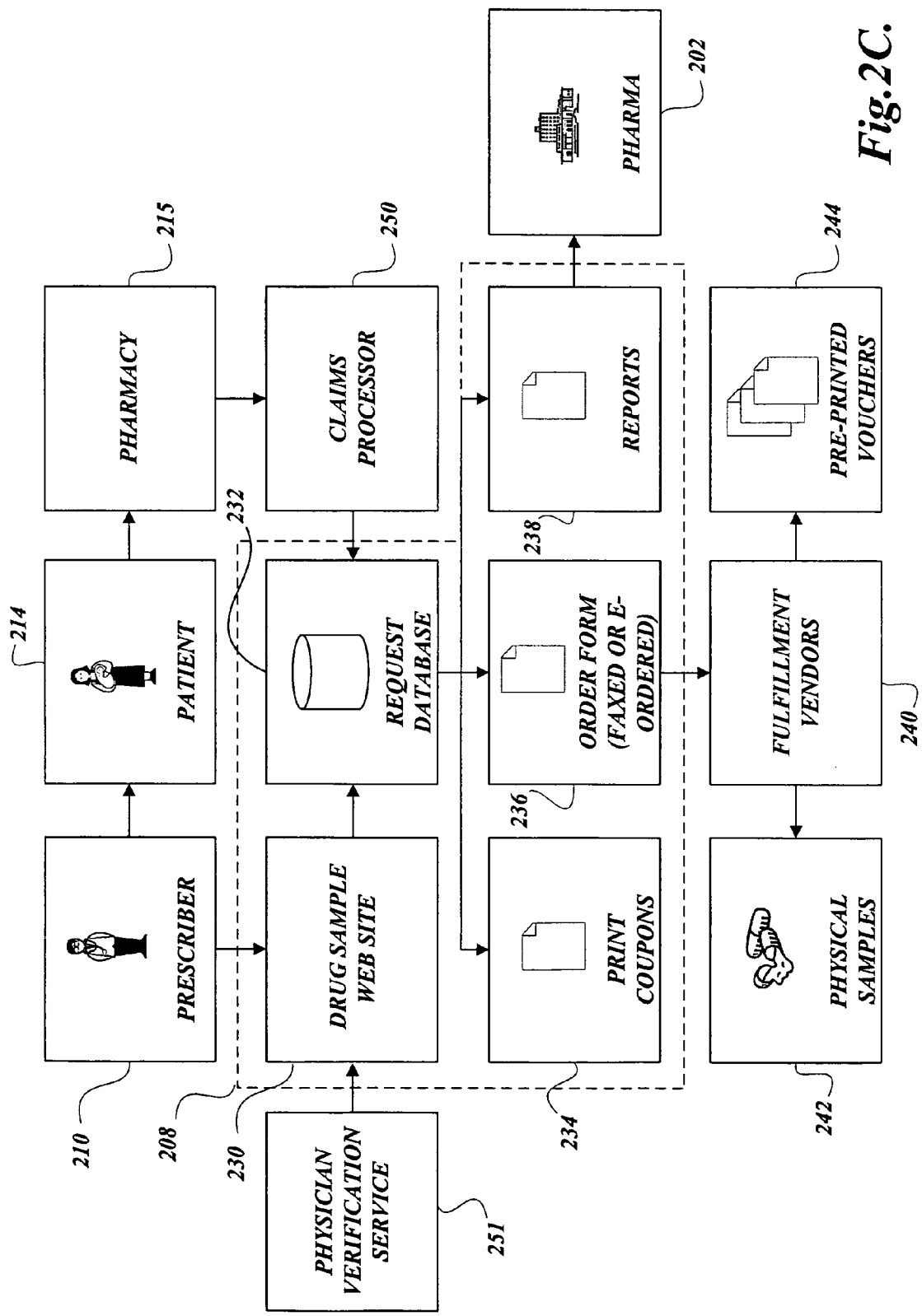
FIG. 2C is a block diagram illustrating pieces of a system for drug sample fulfillment distribution, according to one embodiment of the present invention.

FIG. 2C illustrates another embodiment of the drug sample fulfillment platform 208. The prescriber 210 accesses a drug sample Web site 230 preferably via a Web portal. By selecting a link on the Web portal, the prescriber 210 generates a transaction that includes at least two pieces of information: a prescriber identifier and a partner identifier. The prescriber identifier uniquely identifies the prescriber 210 whereas the partner identifier identifies the Web portal from which the prescriber 210 selects the link to connect to the drug sample Web site 230.

The drug sample Web site 230 produces Web pages that conform to the look and feel of the Web portal with the particular partner identifier. The prescriber identifier will be used by the drug sample Web site 230 to consult with the request database 232 to determine whether the prescriber 210 has visited the drug sample Web site 230 before. If the prescriber identifier is not stored in the request database 232, then it is the prescriber 210's first visit to the drug sample Web site 230. The drug sample Web site 230 will cause the prescriber 210 to undergo a registration process. Among other information, the drug sample Web site 230 asks the prescriber 210 for his name, his individual DEA number, his work address, his medical state license number, his specialty, his e-mail address, his phone, his fax number, and whether the prescriber 210 desires to have his name forwarded to a partner Web site that may provide further drug information, among other pieces of information. The prescriber 210 need not provide all of these pieces of information, because the drug sample Web site 230 can communicate with the prescriber-oriented Web portal to pull various pieces of information already associated with the prescriber 210. This registration process is preferably run only once for a particular prescriber 210.

A second registration process available through the drug sample Web site 230 is related to the registration of the prescriber for an online, electronic drug sample ordering service. If the prescriber 210 wishes to register and create an account for online ordering of drug samples, the prescriber 210 must first be authenticated. A Web page is produced that requests certain authentication descriptors that are descriptive of the prescriber. The Web site 230 will then send the information to the PVS 251, which will compare the authentication descriptors supplied by the prescriber against prescriber information from any selected reliable sources, such as professional associations, such as the AMA, state medical licensing boards, credit bureaus, and the like. When a selected set of authentication descriptors provided by the prescriber 210 match with the records maintained by the PVS 251, then the prescriber 210 is considered to be authenticated and is asked to enter a User ID and a strong password that will be used for later signing drug sample requests with an electronic signature. Otherwise, if the prescriber 210 has not entered a sufficient number of correct authentication descriptors, the prescriber 210 may be given additional attempts to provide the correct information. After the prescriber 210 has successfully completed registration, the prescriber 210 may return to the home page of the Web site 230. Although the present invention may be discussed in the context of authenticating a prescriber using AMA records and state medical licensing records, it is to be understood that other prescribers that are not physicians may also be authenticated in accordance with this invention. In the case of non-physician prescribers, the authentication process may use entities particular to the prescriber's profession or education or any other provider of prescriber information. When using generally less reliable sources of prescriber information, the number of authentication descriptors required from a prescriber may be increased before authentication may be given. Alternatively, there may be a weight assigned to each authentication descriptor, and when a sufficient number of "points" are reached, the prescriber may be authenticated.

Once the prescriber 210 has registered with the drug sample Web site 230, the drug sample Web site 230 will generate a personalized list of drug samples that are available to the prescriber 210 to obtain. In terms of services that can be provided to prescribers in addition to requesting drug samples, prescribers can be provided with information with respect to drugs, continuing medical education, peer forums and conferences, and access to reports on adverse drug reactions from the Web sites of pharmaceutical companies, and from the FDA. Upon exiting the drug sample Web site 230, the prescriber 210 is returned to the Web page of the Web portal from which the prescriber 210 linked to the drug sample Web site 230. During registration, the prescriber 210 is asked to select whether he is interested in receiving future drug samples (via a therapeutic class interest survey) to treat an existing or a new therapeutic class. If he elects to receive future drug samples, when these drug samples become available the prescriber 210 will be notified when the prescriber 210 returns to the drug sample Web site 230.

The prescriber 210, depending on the brand rules 206 specified by the brand manager 204, can access a combination of three sample forms including physical samples 242, pre-printed vouchers 244, and print coupons 234. The physical samples 242 are drug samples that are pre-packaged by the pharma 202 and shipped by a single brand manager-designated fulfillment vendor 240. The prescriber 210 can also order pre-printed vouchers 244, which are pre-printed pads of coupons. These coupons are picked, packed, and shipped to the prescriber 210 via the fulfillment vendors 240 (which may or may not be the same vendor which distributes physical samples). The print coupons 234 are those coupons that prescriber 210 prints in his office. The prescriber 210 can then sign the coupon and give the signed coupon to the patient 214.

To obtain either physical samples 242 or pre-printed vouchers 244, the prescriber 210 prints an order form from the drug sample Web site 230 via the request database 232, signs the order form, and faxes it to one or more fulfillment vendors 240. The pharma 202 can specify a fulfillment vendor 240 (whose fax number is printed on the order form) to which the prescriber 210 faxes the signed order form to obtain physical samples 242 and/or of pre-printed vouchers 244 as applicable. Alternatively, the prescriber 210 may use the online drug sample ordering service, provided that the prescriber 210 has been authenticated and has opened an account. In this alternative method of ordering drug samples via the Web site 230, rather than having the prescriber 210 print the order, sign, and fax the order to the drug sample fulfillment vendor 240, the prescriber 210 may simply enter a User ID, which may be the state medical license number and a previously selected strong password, and the drug sample request order form 236 is transferred online over the Internet to the one or more fulfillment vendors 240. The pharma 202 can specify a fulfillment vendor 240 (whose fax number is printed on the order form) to which the prescriber 210 faxes the signed order form to obtain physical samples 242 and/or pre-printed vouchers 244, as applicable. Alternatively, the order form 236 may be transferred online. The order form 236 is first presented electronically to the prescriber 210 for the prescriber 210 to specify different drug samples that he is interested in. The order form 236 is also personalized to a particular prescriber 210 and a particular fulfillment vendor 240 in accordance with brand rules 206.

The drug sample fulfillment platform 208 is designed to work with any contracted prescriber-oriented Web portal which the prescriber 210 may use, any fulfillment vendor 240 that the pharma 202 wishes to work with via an application specific messaging protocol, and any PVS 251 or other information provider that can provide reliable information on the prescriber. The prescriber 210 may order drug samples that may have to be fulfilled by two fulfillment vendors 240. The drug sample Web site 230 manages such a situation by printing one order form to be faxed to a particular fulfillment vendor and another order form to be faxed to a second fulfillment vendor. Alternatively, if the prescriber 210 is ordering the drug samples online electronically, the order form 236 may first have to be parsed before being sent over a communication network to the one or more fulfillment vendors 240. It is also possible that the prescriber may have to print, sign and fax one order for one fulfillment vendor, while electronically ordering from a second fulfillment vendor. The drug sample fulfillment platform 208 removes the complexity of ordering drug samples for the prescriber 210 while reducing or eliminating mistakes (e.g., errors due to unreadable handwriting). If the prescriber 210 still chooses to fax the drug sample order 236, even if the signed order form 236 is somehow misplaced or lost, the prescriber 210 can print it out again (via the history reprint function) from the drug sample Web site 230 and fax the signed order form to the fulfillment vendors 240 to obtain the desired drug samples. The online drug sample ordering feature does not require elimination of the fax version of the order form 236. The prescriber 210 is given the choice of selecting one or the other mode of sending the order form 236.

Upon receiving physical samples 342, pre-printed vouchers 244, or print coupons 234, the prescriber 210 can provide a combination of those sample forms to the patient 214 to redeem for free medications at the pharmacy 215. When the patient 214 comes to the pharmacy 215 to redeem sample forms for drug samples, the pharmacy 215 forwards the claim to a claims processor 250. The claims processor 250 decides whether to approve the claim. If the claim is approved, the pharmacy 215 provides the desired drug samples to the patient 214 free of charge.

The request database 232 stores for each prescriber 210 identification and the quantity of drug samples that were ordered. The drugs and quantity ordered is compared with the allocation limits for a particular prescriber. This can be presented to the prescriber 210 via the drug sample Web site 230 so that the prescriber 210 knows how many more drug samples the prescriber 210 can order. These pieces of information, among others, are stored by the request database 232. The information in the database can be correlated when the patient 214 takes a pre-printed voucher 244 or a print coupon 234 and redeems it at the pharmacy 215. These pieces of information can be analyzed and explained to the pharma 202 via one or more reports 238. For example, suppose a print coupon was redeemed on a particular date by the patient 214. The reports 238 can indicate when the coupon was redeemed by the patient 214. Moreover, the reports 238 can show whether there is a correlation between a drug sample fulfillment distribution program as specified by the brand rules 306 and the prescribing trend of the prescriber 210.

Figure 3A:
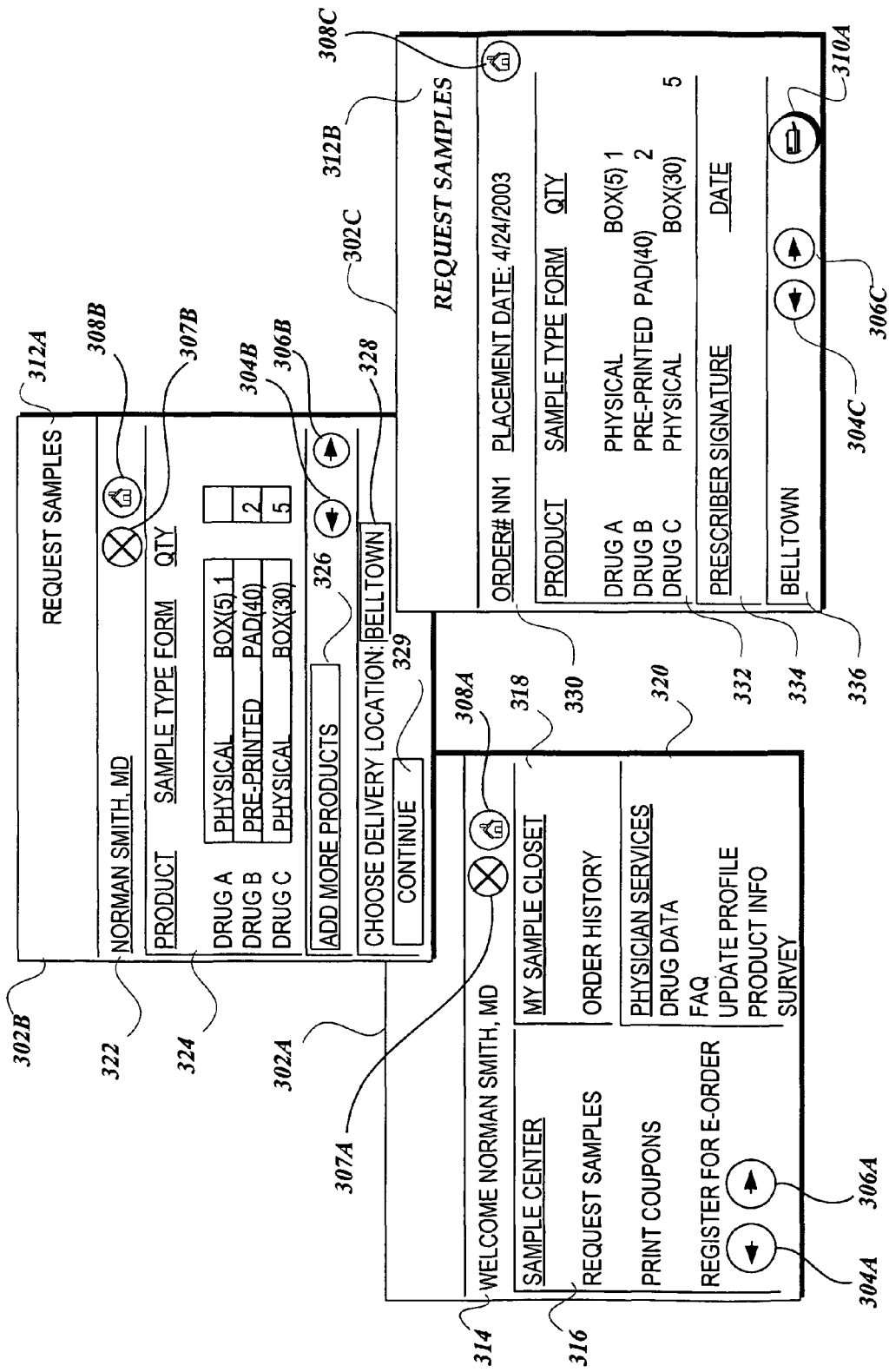
FIG. 3A is a pictorial diagram illustrating various Web pages associated with the drug sample fulfillment platform, according to one embodiment of the present invention.
Figure 3B:
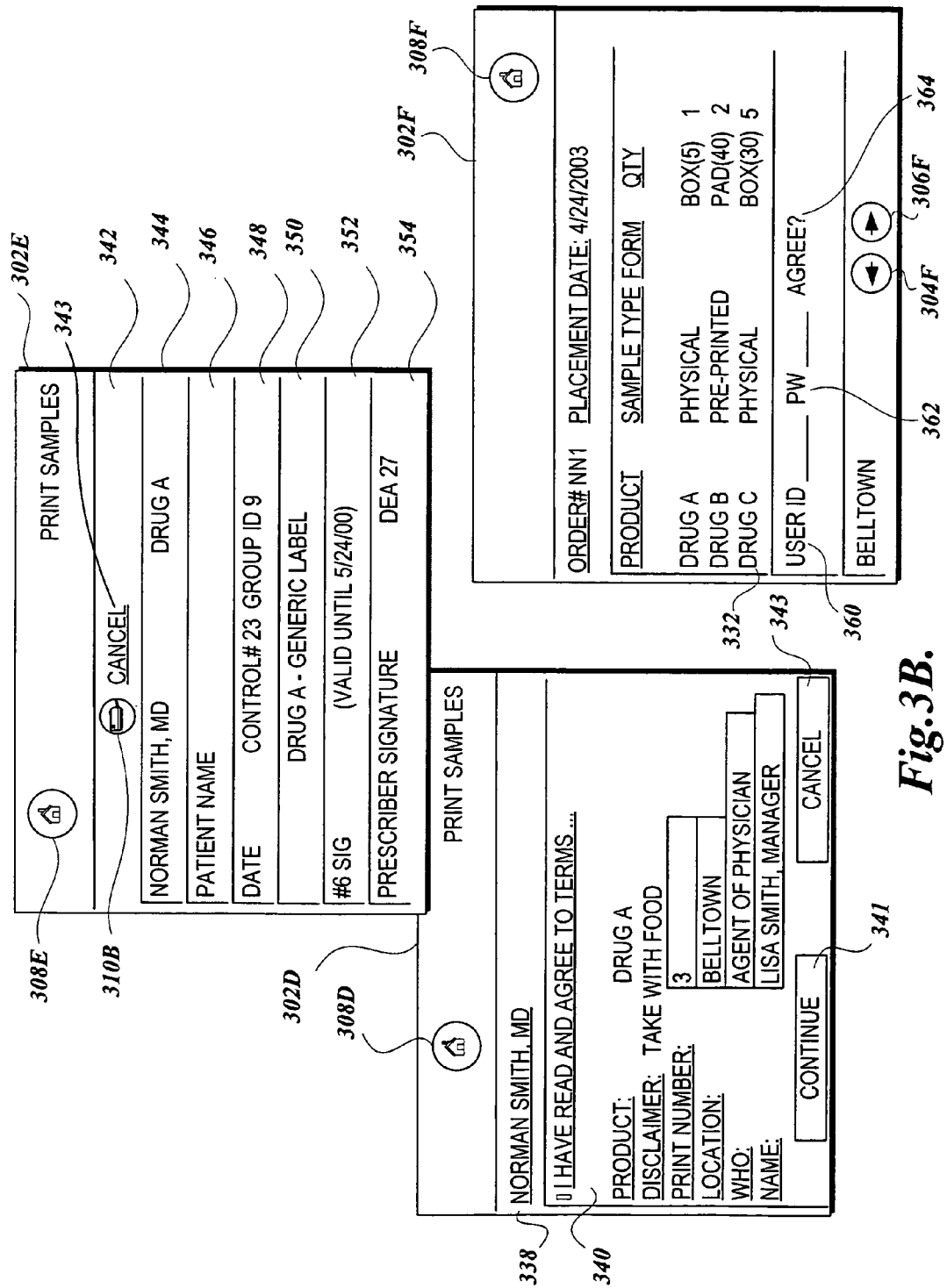
FIG. 3B is a pictorial diagram illustrating various Web pages of a drug sample fulfillment distribution platform, according to one embodiment of the present invention.

Various exemplary Web pages comprising the drug sample Web site 230 are illustrated at FIG. 3A and FIG. 3B. Web pages 302A-302F are navigated by a set of application built navigational buttons/links/tabs, such as PREVIOUS/CANCEL buttons 304A-304F, NEXT/CONTINUE/CONFIRM buttons 306A 306F, and HOME buttons 308A-308F. These buttons appear in standard locations on Web pages 302A-302F throughout the application. Regarding the Web page 302A, a greeting 314 "WELCOME NORMAN SMITH, M.D." identifies the prescriber 210. A set of "SAMPLE CENTER" links 316 allows the prescriber 210 to access various sample services, such as "REQUEST SAMPLES"; "PRINT COUPONS"; and "REGISTER FOR E-ORDER." A notice 307A may be placed on the title bar 314 to instantly notify the prescriber 210 whether the prescriber 210 is in e-order enabled mode, and the prescriber 210 may order drug samples online, or whether the prescriber 210 is in e-order non-enabled mode, and the prescriber must sign and fax the drug sample order. The notice 307A may have an "X" to indicate not enabled, and no "X" to indicate enabled. In the example, the prescriber 210 is not enabled or order online. "E-order" is shorthand for "electronic order" and is a way of quickly expressing the electronic, online drug sample ordering aspect of the invention. If the prescriber 210 is already enabled for e-ordering, the link to "REGISTER FOR E-ORDER", may not appear. A set of "MY SAMPLE CLOSET" links 318 allows the prescriber 210 to view what drug samples are available as well as a history of previous orders. A set of "PHYSICIAN SERVICES" links 320 allows the prescriber 210 to access drug data, get answers to frequently asked questions, update his profile, request additional detail support or product information from pharma sales representatives 106, obtain product information online, and therapeutic class survey. A further service available through various embodiments of the present invention includes maintaining "MY SAMPLE CLOSET" for a prescriber. Particular drug products and quantities can be suggested to the prescriber, and then the sample drug closet can be automatically replenished as requested by the prescriber. Also, for sample programs that expire, the system can shut down redemptions through the pharmacy network via the claims processor 250, notify all participating prescribers, and disable all online sample order requests for the specific drug.

Selecting the "REQUEST SAMPLES" link of the set of links 316 brings up an exemplary Web page 302B for the prescriber 210 to request drug samples. A title of the Web page "REQUEST SAMPLES" 312A appears on the menu bar and is flushed to the left for both the Web page 302B as well as the Web page 302C. In the Web page 302B, the prescriber 210 continues to remain not e-order enabled, accordingly, the notice 307B is still crossed out. Regarding the Web page 302B, line 322 identifies the name of the prescriber 210. Area 324 is an array formed from four columns and a number of rows. The first column identifies the product or the drug sample available to the prescriber 210. The second column is the sample type for a particular drug that the prescriber 210 can order. The third column identifies the form in which the drug sample is made available. The fourth column identifies the quantity that the prescriber 210 specifies. The first row of the area 324 indicates that "DRUG A" is available in physical form (or in an alternative form such as pre-printed vouchers) for which there are five samples in a box and that the prescriber 210 has ordered a quantity of one. The second column specifies that the "DRUG B" is available via pre-printed forms (or in an alternative form such as physical samples) for which 40 coupons are available in a pad and that the prescriber 210 has ordered a quantity of two. The third column specifies that drug C is available in physical form (or in an alternative form such as pre-printed vouchers) for which there are 30 samples in a box and that the prescriber 210 has ordered a quantity of five.

The prescriber 210 may select a button 326 "ADD MORE PRODUCTS" to add more drug samples to be ordered. The prescriber 210 also specifies a delivery location at line 328 for which "BELLTOWN" has been selected (other delivery destinations may be possible). When the prescriber 210 is satisfied with the order, he selects a CONTINUE button 329 to prepare a finalized order form for printing, which is represented by the Web page 302C. A PRINT button 310A is available for the prescriber 210 to select to print the finalized order form. Line 330 indicates an order number "NN1" and a placement date "4/24/2003," among other pieces of information. An area 332 is a recap of the area 324 which shows the various drug samples that the prescriber 210 is interested in and the quantity of each that the prescriber 210 is expecting to receive. Area 334 requires the prescriber's signature as well as an execution date of the order form. Area 336 indicates the delivery address to which the samples will be shipped when the order form has been processed by fulfillment vendors 340.

Alternatively, if the prescriber 210 was pre-registered for online drug sample ordering, which would have been indicated by the notices 307A and 307B not having an "X", then a Web page, such as the Web page 302F, would appear when the prescriber finishes selecting the drug samples he or she is interested in receiving, and selects the CONTINUE button 329 on Web page 302B. Web page 302F that appears when the prescriber 210 is enabled to e-order drug samples online is similar in many respects to Web page 302C, and includes the order number "NN1", the placement date "4/24/2003", and an area 332 that is a recap of area 324 which shows the various drug samples that the prescriber 210 is interested in and the quantity of each that the prescriber is expecting to receive. However, in place of a signature field and execution date field as in Web page 302C, the Web page 302F includes a "USER ID" field 360 and a "PASSWORD" field 362, which need to be filled in by the prescriber 210 in order to transmit with the order. The prescriber 210 must select the AGREE button 364 to complete the online drug sample order transaction. The AGREE button 364 is also to certify that the order to be sent to the drug sample fulfillment vendor is the equivalent of an order with a written signature. By selecting the AGREE button 364, the Web page 302F will electronically transfer the drug sample request order to a fulfillment vendor 340 over a communication network.

If the prescriber 210 selects the "PRINT COUPONS" link in area 316 of the Web page 302A, the Web page 302D appears. Line 338 identifies the name of the prescriber 210, which is "NORMAN SMITH, M.D." An area 340 includes a link "I HAVE READ AND AGREE TO TERMS . . . " which allows the prescriber 210 to select and review terms and conditions for printing coupons for certain drug samples. The prescriber must check the box indicating his agreement with the PDMA (Prescription Drug Marketing Act which is a federal regulation prohibiting among other things the copying and/or selling of drug sample vouchers or coupons) guidelines before being allowed to print. The area 340 includes a "PRODUCT" line identifying the drug (DRUG A) for which the prescriber 210 may print coupons. An "Important Information" line specifies important information that the prescriber 210 can review in connection with the selected drug sample. An "INTENT TO PRINT NUMBER" line specifies the number of coupons which the prescriber 210 wishes to print. A "LOCATION" line allows the prescriber 210 to specify the prescriber's address that will be printed on the voucher. A "WHO" line allows the prescriber 210 to specify whether the prescriber 210 is a physician or an agent of the physician. A "NAME" line allows the person printing the coupons to specifically identify herself if she is an agent of the prescriber. Selecting a CONTINUE button 341 brings forth the Web page 302E for the prescriber 210 to review. Selecting a CANCEL button 343 terminates the session.

The content of the Web page 302E is in essence a coupon for the prescriber 210 to dispense to the patient 214. A PRINT button 310B allows the prescriber 210 to select and print out one or more coupons as specified on the Web page 302D. Line 342 allows the prescriber 210 to cancel the printing process. Line 344 identifies the names of the prescriber "NORMAN SMITH M.D." and the drug "DRUG A" to be redeemed by the printed coupon. Line 346 identifies a patient name. Line 348 contains the date that the coupon is given to the patient 214, a carrier number "23" and a group ID number "9" associated with the claim when the coupon is presented at the pharmacy 215. Line 350 identifies the drug to be redeemed by the coupon. Line 352 indicates the dosage. Additionally, an expiration date "5/24/00" is specified on line 352 (a rolling voucher expiration date from date printed or a fixed date as defined by pharma brand rules 206). Line 354 provides space for the prescriber's signature, and the prescriber's DEA number is shown next to an area where the prescriber writes his signature. Further, the printed voucher can be customized by the prescriber to include or not include his office phone number and DEA number.

FIGS. 4A-4L illustrate a method 400 for enhancing a drug sample fulfillment program. For clarity purposes, the following description of the method 400 makes references to various elements illustrated in connection with the drug sample fulfillment platform 208 (FIGS. 2A, 2B, 2C), brand rules 206 (FIG. 2A), the drug sample Web site 230 (FIG. 2C), and Web pages 302A-302E (FIGS. 3A-3B). From a start block, the method 400 proceeds to a set of method steps 402, defined between a continuation terminal ("Terminal A") and an exit terminal ("Terminal B"). The set of method steps 402 describes the commencement of the drug sample fulfillment program by determining a class of prescribers as a target for the drug sample fulfillment program.

From Terminal A (FIG. 4C), the method 400 proceeds to block 414 where the method receives one or more deciles of prescribers to target from the brand manager 304 of the pharma 302. The method 400 also receives one or more criteria to target eligible prescribers as determined by the brand manager 204. See block 416. The method then divides a set of prescribers (from the selected deciles and specialties) into one or more segments according to the brand manager 204. See block 418. At block 420, within each segment, the method 400 specifies a quantity of drug samples to distribute according to the brand manager 204. Next, at block 422, within each segment, the method 400 specifies a combination of sample types or forms (i.e., physical samples, pre-printed vouchers, or print coupons) to be made available to the prescribers 210 according to the brand manager 204. See block 422. Within each segment, the method 400 also specifies a time frame in which the drug samples are made available to the prescribers 210 according to the brand manager 204. See block 424. The method then charges the pharma 202 an implementation service fee for implementing the brand rules as set forth by the brand manager 204. See block 426.

Pharmaceutical companies and their sales representatives have certain rules that they use in determining that prescribers are to be given drug samples in general, as well as which drug samples are to be made available, and the quantity of such drug samples. These rules are established on a prescriber-by-prescriber basis and are in effect when a prescriber requests drug samples. Such rules can be based on many factors, including the specialty of the prescriber, the prescriber's location, the prescriber's age, the prescriber's past history of requesting drug samples and providing such samples to patients, and the prescriber's history in prescribing such drugs. When a prescriber's practice or situation changes, the rules for the prescriber with respect to drug samples provided can also be altered. From here, the method 400 enters the exit Terminal B.

From the exit Terminal B (FIG. 4A), the method 400 proceeds to a set of method steps 404, defined between a continuation terminal ("Terminal C") and an exit Terminal ("Terminal D"). The set of method steps 404 describes the ways in which targeted prescribers 210 request drug samples online via the drug sample fulfillment platform 208.

From Terminal C (FIG. 4D), the method 400 proceeds to block 428 where prescribers 210 are recruited to participate in the drug sample fulfillment program via prescriber-oriented portals, prescriber recruiting services, and/or e Detailing providers. Other suitable recruitment techniques are possible, such as by telephone or fax. A recruited prescriber 210 is authenticated when he logs into a portal or a Web site giving access to the drug sample fulfillment platform 208. See block 430. This prescriber 210 selects a link on the portal giving him access to the drug sample fulfillment platform 208. See block 432. A transaction is generated when the link is selected that includes a prescriber identifier and a partner identifier and these are forwarded to the drug sample fulfillment platform 208. See block 434. Based on the partner identifier, the drug sample fulfillment platform 208 tailors the Web pages in order to emulate the look and feel of the prescriber-oriented portal. See block 436. The application specific messaging protocol allows the prescriber-oriented portal to open the sample fulfillment platform 208 within a frame allowing the prescriber 210 to navigate Web pages. See block 438. The method then enters another continuation terminal ("Terminal C1").

From Terminal C1 (FIG. 4E), the method 400 proceeds to decision block 440 where a test is made to determine whether the prescriber 210 is in the request database 232. If the answer to the test at decision block 440 is NO, the method 400 proceeds to block 442 where the drug sample fulfillment platform 208 causes the prescriber 210 to complete a registration process requiring information such as name, DEA number, medical state license number, etc. The method 400 proceeds next to block 445 from block 442. If the answer to the test at decision block 440 is YES, the method 400 also enters block 445. At block 445, the method 400 announces whether the prescriber 210 is enabled to electronically order drug samples. The registration process for electronically placing drug sample orders may have been completed in an earlier session or in the same session, but at an earlier time. If the prescriber 210 is not in the database, the method 400 may prompt the prescriber 210 to subscribe to the electronic drug sample ordering service, and complete an authentication routine for prescriber 210 online. After successfully completing registration for electronic ordering, the method 400 proceeds to block 444. Even if the registration process for electronic ordering was not successful, i.e., because of lack of authentication, the prescriber 210 may still order drug samples via printing and faxing the order form to the fulfillment vendors. When the prescriber 210 is enabled to electronically order sample drugs online, the Web pages produced by the drug sample fulfillment platform 208 may have features and links specifically related to the electronic ordering aspect.

The method 400 determines drug samples that are available to the prescriber (who belongs to a certain segment of prescribers). See block 444. At block 446, the method 400 determines a sample quantity limit for each drug sample that is available to the prescriber 210. At block 448, the method 400 determines a sample time limit for each drug sample that is available to the prescriber. For example, a particular drug is available to a prescriber for a limited duration beyond which he cannot order more. Next, the method 400 determines the type or form of sample that is appropriate for each drug sample that is available to the prescriber 210. See block 450.

Various embodiments of the present invention can also take into consideration certain preferences of a prescriber, such as printing DEA and/or office telephone numbers on the print on-demand voucher. The method 400 then enters another continuation terminal ("Terminal C2").

From Terminal C2 (FIG. 4F), the available drug samples and its forms are presented to the prescriber 210 via an application specific messaging protocol. See block 452. Next, at decision block 454, a test is made to determine whether the prescriber selected physical samples. If the answer is NO, another test is made at decision block 456 where it is determined whether the prescriber 210 selected pre-printed vouchers. If the answer to the test at decision block 454 or 456 is YES, the method 400 enters block 458. The prescriber 210 selects the drug samples that he is interested in on the Web page 302B. See block 458. Next, at block 460, the prescriber 210 selects the sample types (physical samples or pre-printed vouchers) available for the selected drug samples and quantity. See Web page 302B. The method 400 enters another continuation terminal ("Terminal C3").

If the answer to the test at decision block 456 is NO, the method 400 enters another continuation terminal ("Terminal C4").

From Terminal C3 (FIG. 4G), the method 400 proceeds to block 462 where the prescriber 210 selects a delivery address to which the physical samples or the pre-printed vouchers will be sent. See Web page 302B. Next, at decision block 463, a test is made to determine whether the prescriber 210 is enabled to order drug samples online. If the answer to the test at decision block 463 is YES, the method enters block 465, where the prescriber 210 enters a User ID, such as the state medical license number, a state of licensure, and a suitably strong password, and certifies that the User ID and password are the equivalent of a signature. See Web page 302F (FIG. 3B). The drug sample order is sent over a communication network to the fulfillment vendor, in real time, and without having to print, sign, and fax the order to the fulfillment vendor. The method then bypasses blocks 464 and 466 and proceeds to block 468, where the prescriber 210 receives the order from the fulfillment vendor. If the answer to the test at decision block 463 is NO, then the method enters block 464, where, the prescriber prints out the sample request order and signs the sample request order in one embodiment. In another embodiment, he need not sign the sample request order if it is for pre-printed vouchers 244. See block 464 (see also the Web page 302C). Next, at block 466, the prescriber 210 faxes the signed sample request order 236 to a fulfillment vendor 240 in accordance with the instructions on the sample request order 236. The prescriber 210 receives the order from the fulfillment vendor 240, also upon entering block 468. The requesting activities of the prescriber 210 are then recorded in the request database 232. The method 400 then enters the exit Terminal D.

From Terminal C4 (FIG. 4H), the method 400 proceeds to block 472 where the prescriber 210 selects the drug samples for which he is interested in printing out coupons. The coupons that are printed by the prescriber are dynamically built at the time requested so as to include the prescriber's name and address, the particular drug requested, the strength of the drug, the expiration date of the voucher, the prescriber's DEA number, and the trademark and logo not only of the drug, but also of the drug manufacturer. The method 400 then enters another continuation terminal ("Terminal C5").

From Terminal C5 (FIG. 4I), the method 400 proceeds to block 474 where the method 400 presents the maximum number of coupons the prescriber can print. The prescriber selects the number of coupons to be printed. See block 478 (see also the Web page 302D). The prescriber 210 then specifies whether a physician is printing coupons or whether an agent of the physician is printing them. See block 480 (see also the Web page 302D). If the agent is printing the coupons, the name of the agent is requested by the method 400. See block 482. The prescriber then prints out the number of coupons. See block 484. The method 400 then enters the exit Terminal D.

From the exit Terminal D (FIG. 4A), the method 400 proceeds to a set of method steps 406, defined between a continuation terminal ("Terminal E") and an exit terminal ("Terminal F"). The set of method steps 406 describes the act of giving physical samples to patients by targeted prescribers 210 or patients 214 redeeming pre-printed vouchers or print coupons at pharmacies.

From Terminal E (FIG. 4J), the prescriber 210 gives the patient 214 physical samples, pre-printed vouchers, print coupons, or all of these. See block 486. The patient 214 redeems the pre-printed vouchers or print coupons at the pharmacy 215. See block 488. A claim is entered into the computer system at the pharmacy 215, and a clearinghouse, such as a pharmacy benefit manager, approves the claim. See block 490. If the claim is approved, the patient 214 receives the physical samples for free. See block 492. The clearinghouse then forwards claim data to the request database 232, where it is stored for later analysis. See block 494. The method 400 then enters the exit Terminal F.

From Terminal F (FIG. 4A), the method 400 proceeds to another continuation terminal ("Terminal F1"). From Terminal F1 (FIG. 4B), the method 400 proceeds to a set of method steps 408, defined between a continuation terminal ("Terminal G") and an exit terminal ("Terminal H"). The set of method steps 408 describes the commencement of the generation of reports and fraud detection is enabled.

From Terminal G (FIG. 4K), the method 400 proceeds to block 496, where the prescriber data, the request data, and the claim data are extracted from the request database 232. See block 496. The method 400 then proceeds to block 498 where the method 400 prepares standard and custom reports for the pharma 202. There are three types of reports that are possible. One report lists sample demand statistics. For example, the number of drug samples requested by a certain prescriber can be reported. As another example, the number of vouchers or coupons that were redeemed by patients of a particular prescriber can also reported. The second type of report provides promotional response analysis. For example, the correlation of the requested drug samples and the prescribing behavior of a particular prescriber is described. The third type of report focuses on return on investment analysis. For example, the pharma 202 spends a certain amount of money in connection with the drug sample fulfillment program managed by the brand manager 204. The number of prescriptions for the same drug by a certain prescriber can be correlated with the spending of the pharma 202 to generate potential return on investment analysis.

Through the process described above, certain information is captured, including the name of the prescriber, the date of the redemption of the coupon, the identity of the drug sample given, as well as certain information about the patient, but without identifying the patient. This information is made available to the pharma 202 so that vouchers and coupons for sample medications distributed by prescribers can be tracked. The pharma 202 can also obtain information as to the prescribing of the drug in question by a prescriber through the request database 232. In this manner, the pharma 202 can evaluate the effectiveness of providing drug samples to a prescriber, including how often the prescriber prescribes that same drug. This enables the pharma 202 to make determinations, including not only the success of its sample program generally, but also with respect to continuing to make samples of the drug available to the prescriber. The reported information can also be used to identify prescribers who would be good targets for new drugs being introduced by pharmaceutical companies or good candidates for drug focus groups, as well as perhaps for other products and services of interest to prescribers. Lastly, these reports can be utilized by sales representatives for the purpose of generating and distributing sample vouchers to their targeted prescriber clientele.

The information generated in these reports also aids in fraud analysis. For a given prescriber, an allocation limit for drug samples associated with that prescriber is known. Moreover, the time frame in which those drug samples are valid is also known and specified in the brand rules 206 by the brand manager 204. Based on the redemptions that come in via the claim data provided by the claim processor 250, fraud analysis can determine whether more vouchers or coupons were redeemed within the time frame limit than had been allocated. If there is an inconsistency between the allocation limit and the number of redeemed vouchers or coupons by patients, a flag is raised for further investigation. Preferably, the pre-printed vouchers and print coupons contain the prescriber's DEA number or other identifying indicia for accurate fraud detection analysis. The method 400 then enters the exit Terminal H.

From Terminal H (FIG. 4B), the method 400 proceeds to a set of method steps 410, defined between a continuation terminal ("Terminal I") and an exit terminal ("Terminal J"). The set of method steps 410 describes the payment calculation for each drug sample fulfillment transaction.

From Terminal I (FIG. 4L), the method 400 proceeds to block 499, where the pharma 202 is charged a reporting fee for the preparation of the reports generated in the set of method steps 408. For each request for a sample from a prescriber, the pharma 202 is also charged a transaction request fee. See block 497. The pharma 202 is also charged a sample voucher redemption fee for each successful redemption of a print coupon or a pre-printed voucher by the patient 214. See block 495. Not shown is an annual fee charged to the pharma 202 for the use of the drug sample fulfillment platform 208 and the maintenance of the drug sample fulfillment platform 208. Software updates as well as customization of various brand rules specified by the brand manager fall under this fee. The method 400 then enters the exit Terminal J.

From Terminal J (FIG. 4B), the method 400 proceeds to a set of method steps 412, defined between a continuation terminal ("Terminal K") and an exit terminal ("Terminal L"). The set of method steps 412 describes the commencement of the refining of the drug sample fulfillment program to enhance the ability of certain prescribers 210 to access drug samples.

Figure 4A:
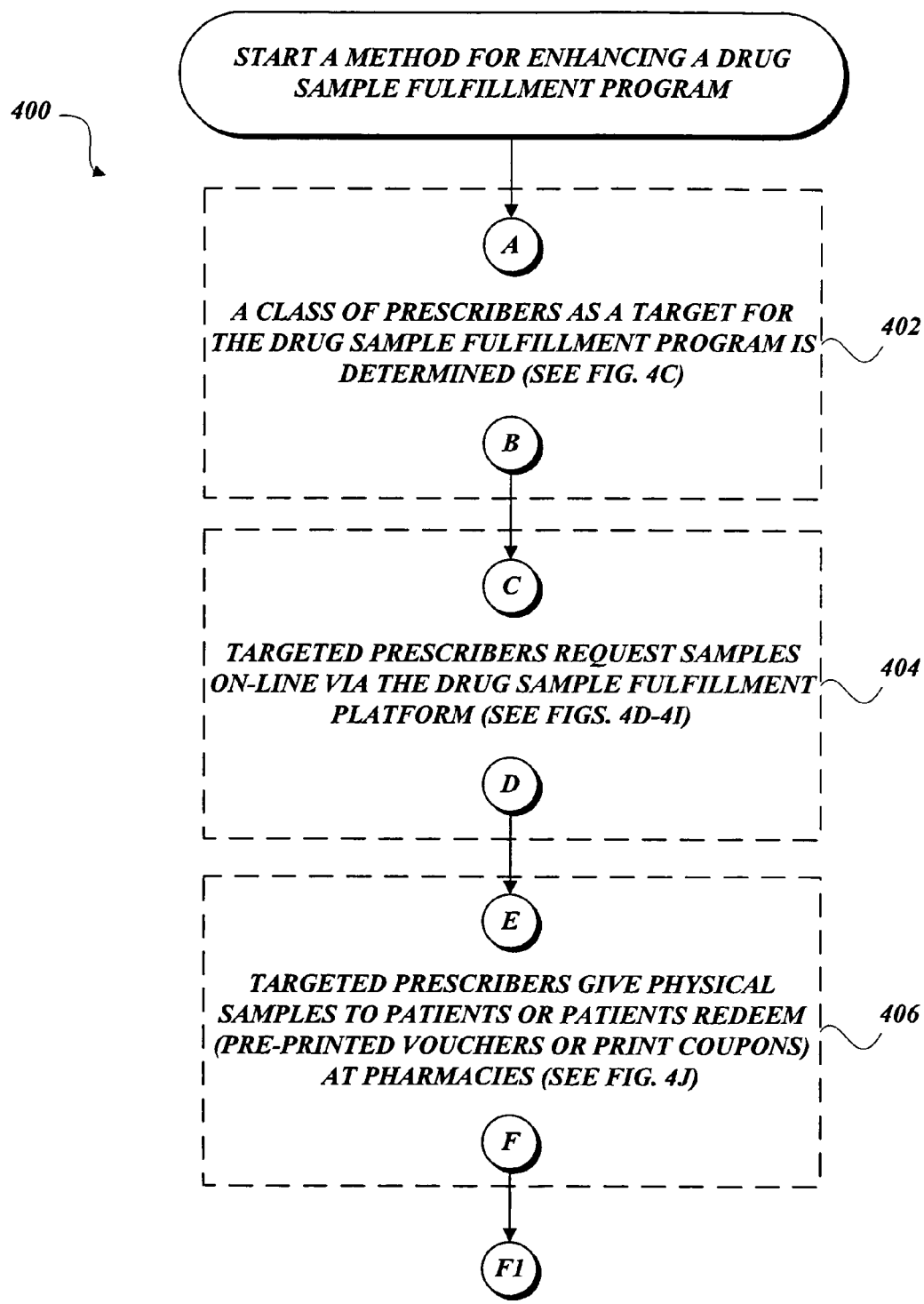
Figure 4B:
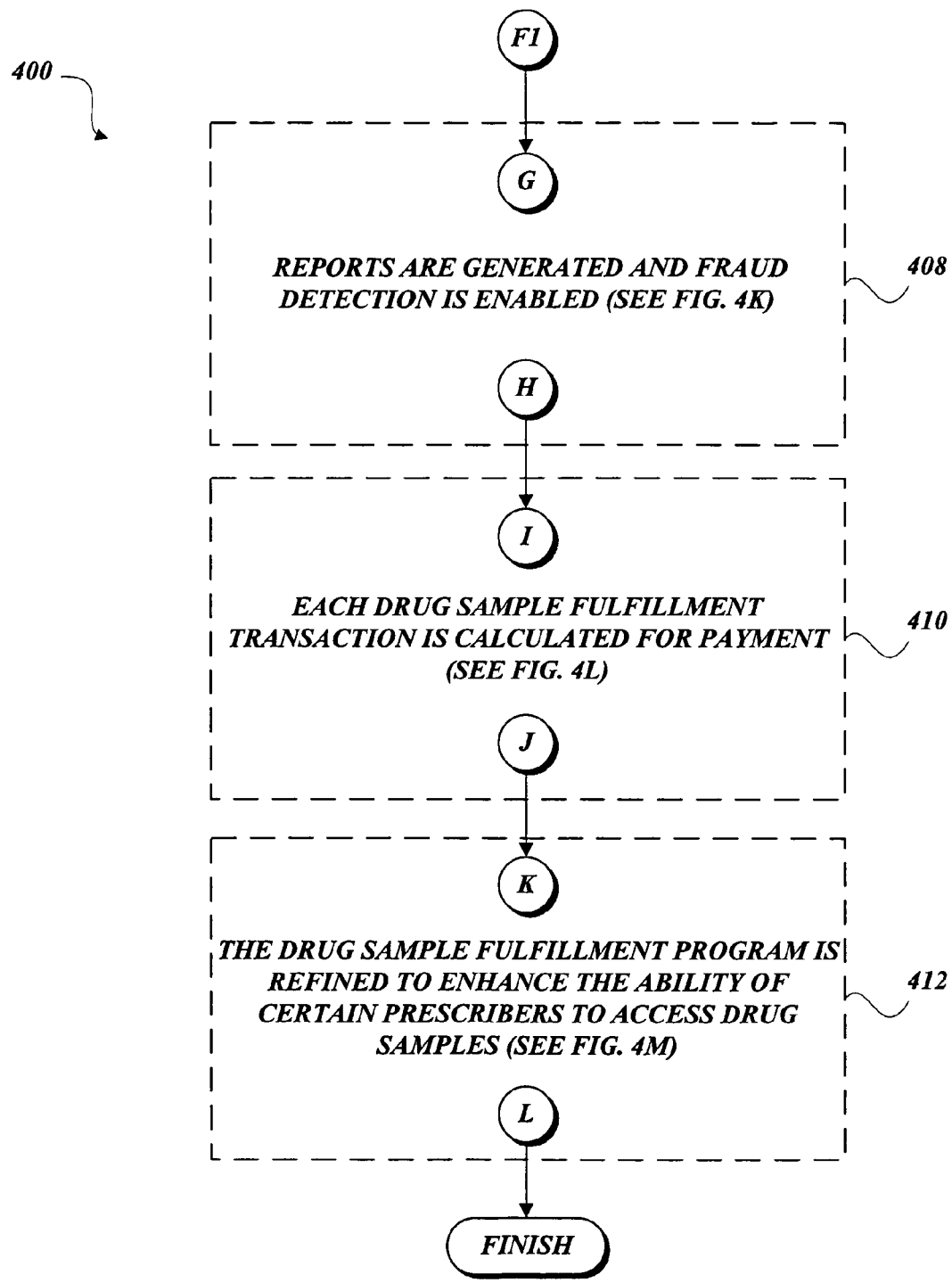
Figure 4C:
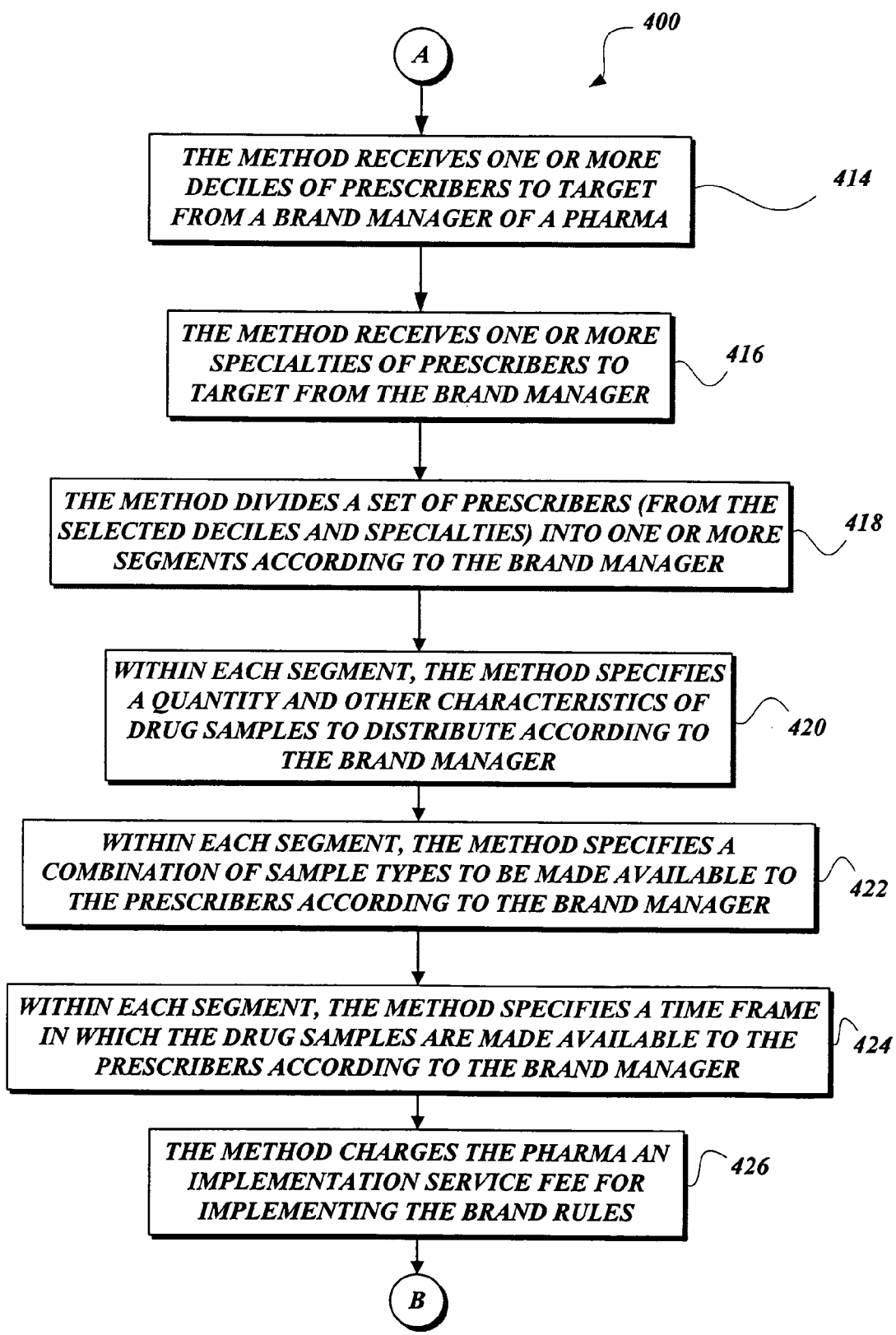
Figure 4D:
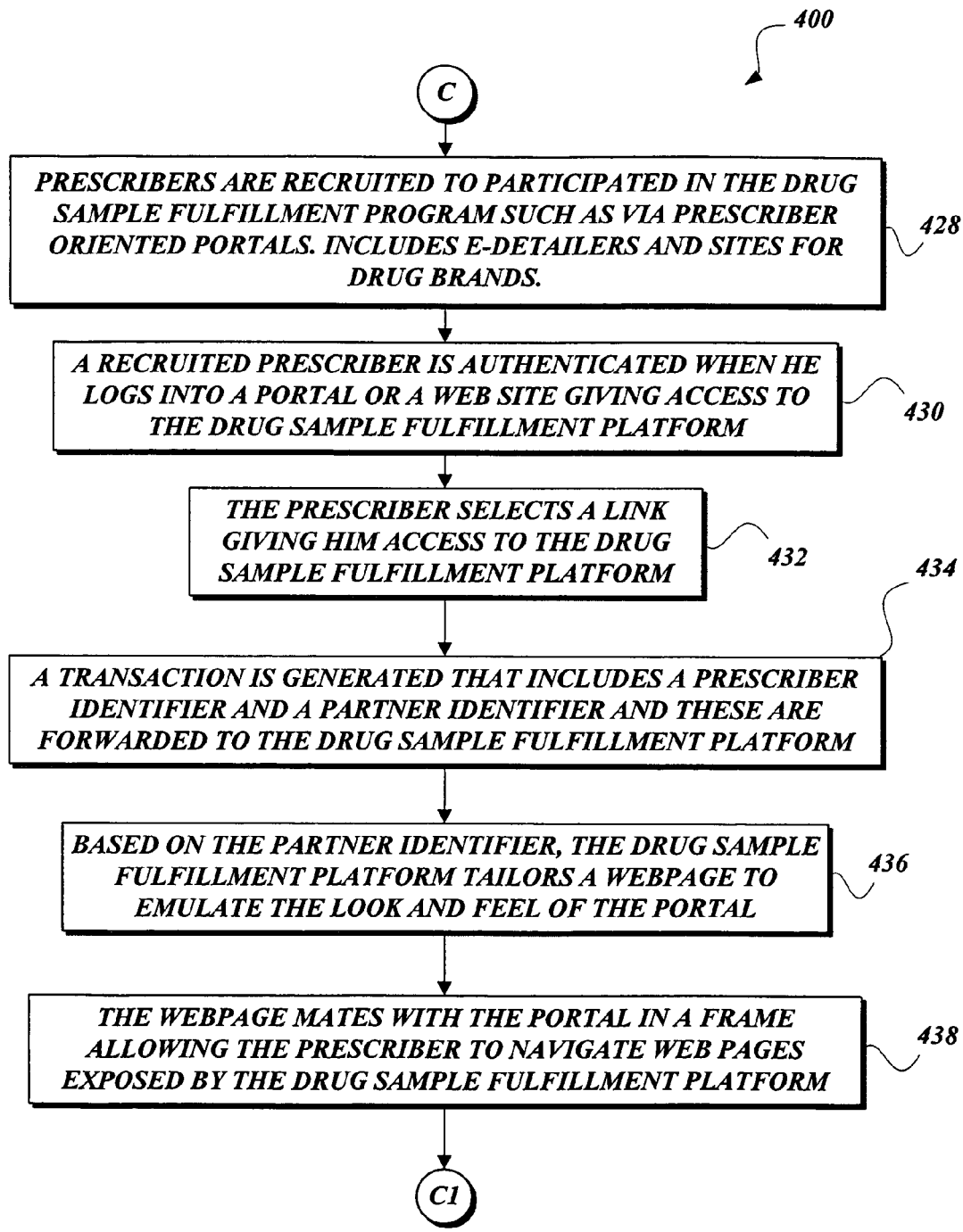
Figure 4E:
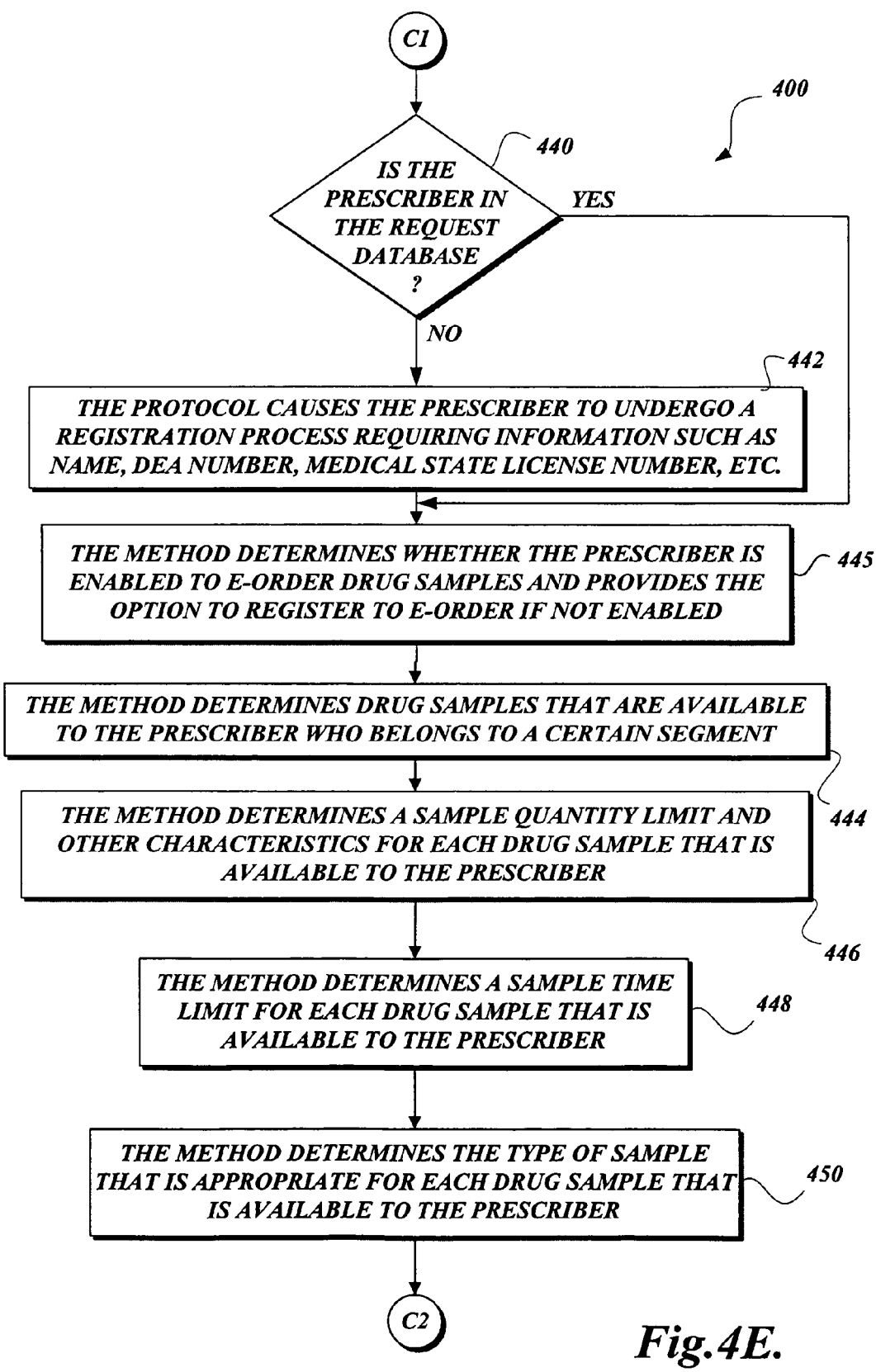
Figure 4F:
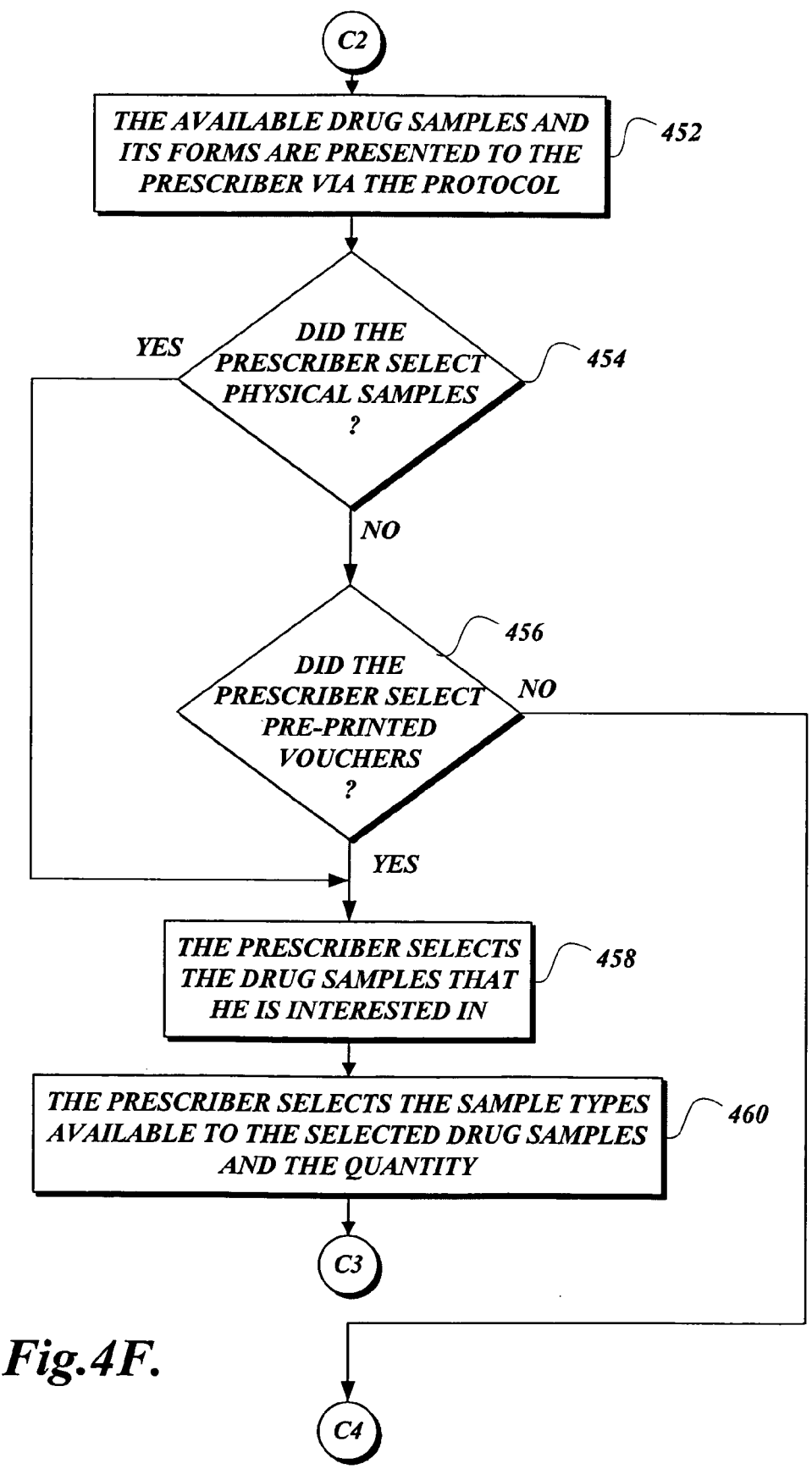
Figure 4I:
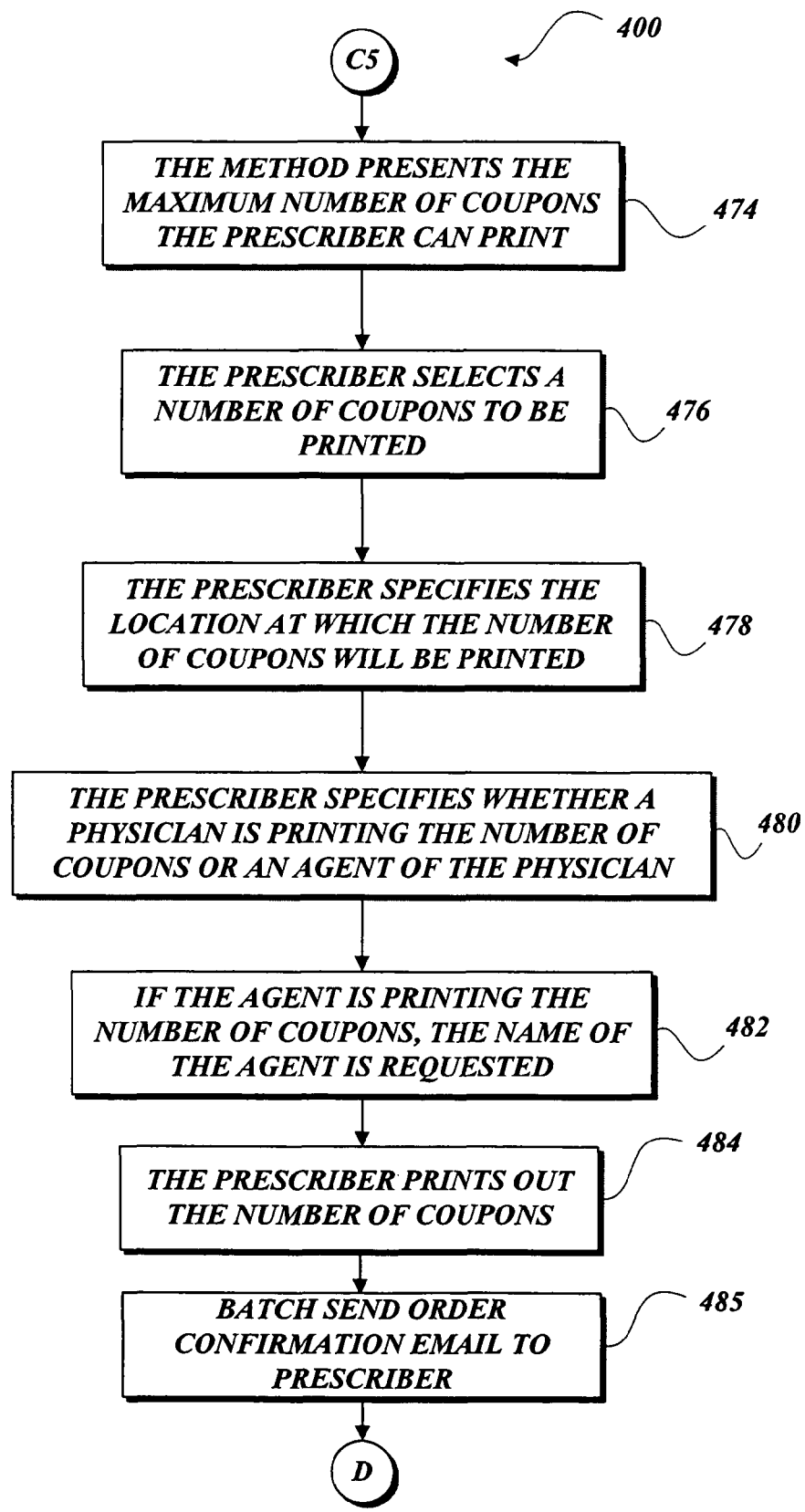
Figure 4J:
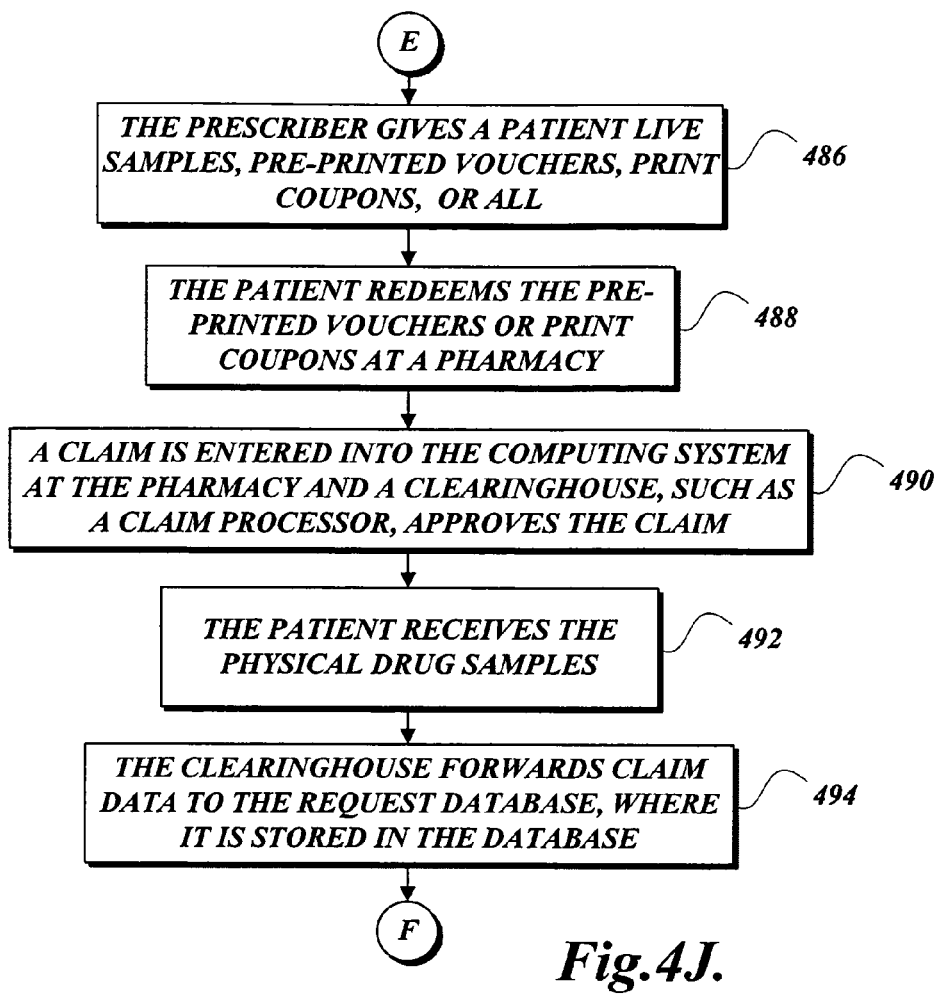
Figure 4K:
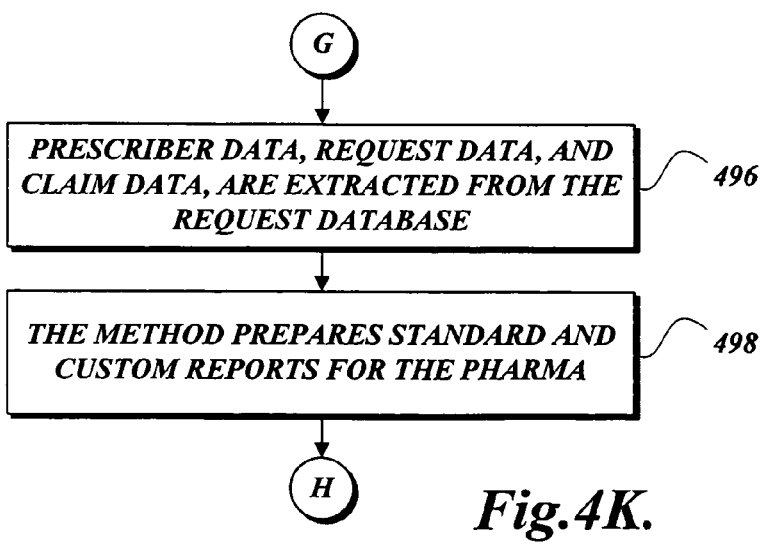
Figure 4L:
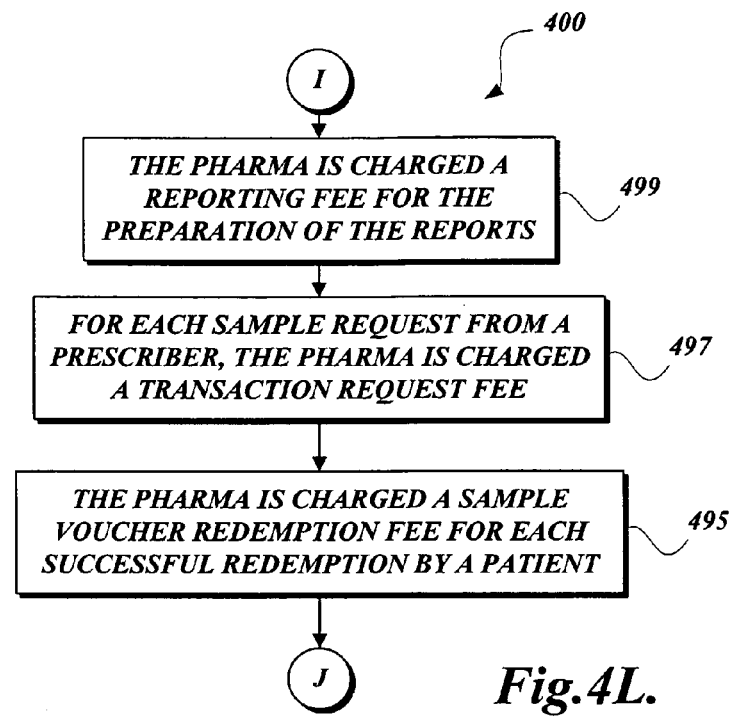
Figure 4M:
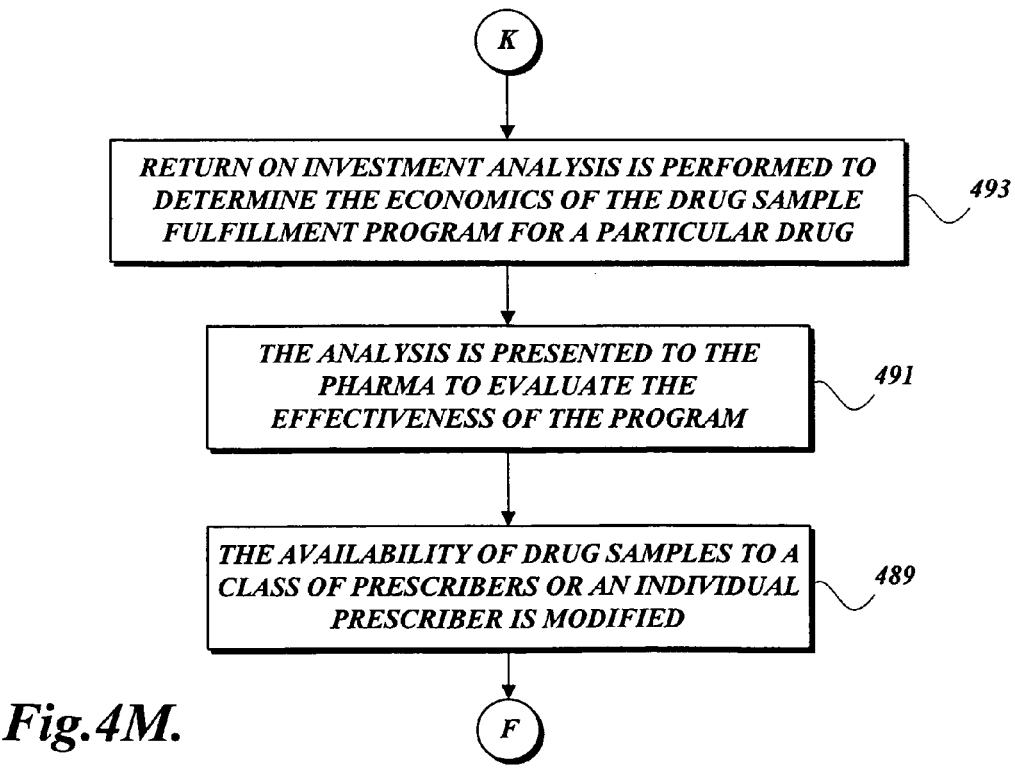

From Terminal K (FIG. 4M), the method 400 proceeds to block 493 where a return on investment analysis is performed to determine the economics of the drug sample fulfillment program for a particular drug. The analysis is then presented to the pharma 202 to evaluate the effectiveness of the program. See block 491. The availability of drug samples to a class of prescribers 210 or an individual prescriber is then modified. See block 489. From there the method 400 proceeds to the exit Terminal F and finishes execution.

Figure 5:
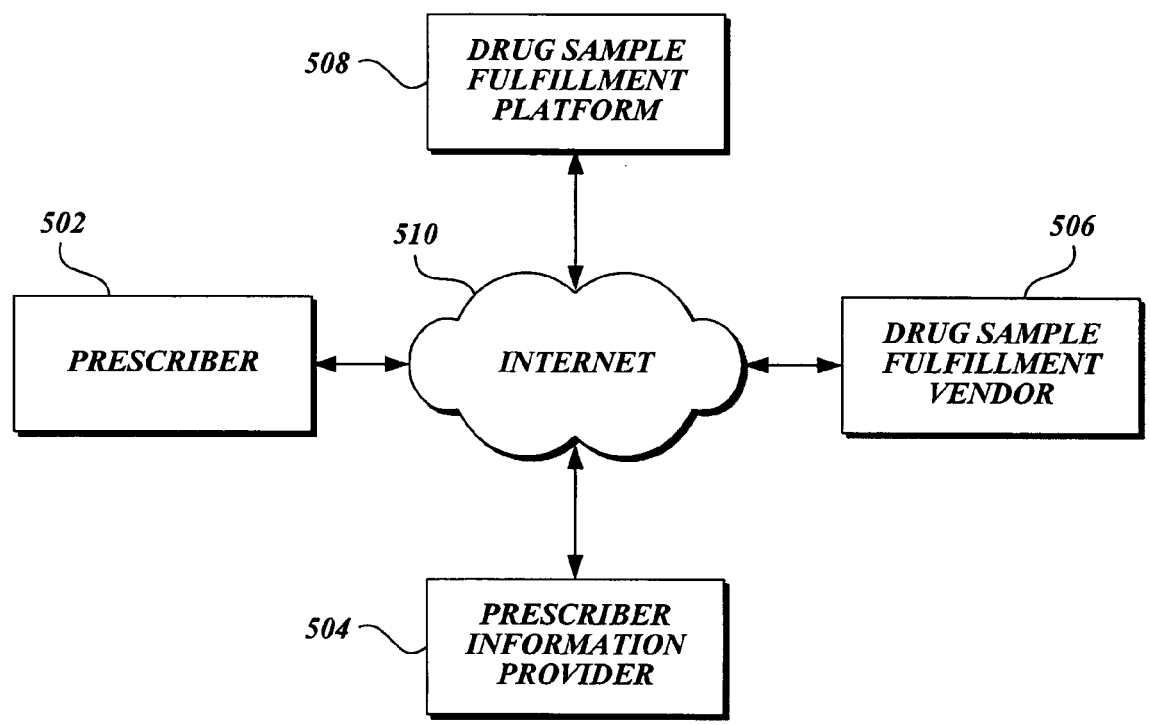
FIG. 5 is a pictorial diagram illustrating an environment for authenticating a prescriber over a communication network, according to one embodiment of the present invention.

Referring now to FIG. 5, a representative system for authenticating a prescriber in real time, over a communication network, is illustrated. The system depicted in FIG. 5 enables communications between a prescriber 502, the drug sample fulfillment platform 508, an information provider 504, and a drug sample fulfillment vendor 506. Each of the entities employs the use of a computer or computer system, such that each computer or computer system is communicatively connected via a communication network 510 to each other.

The prescriber 502 includes, but is not limited to, physicians, physician assistants, certified registered nurse practitioners, advanced registered nurse practitioners, and other licensed professionals authorized to prescribe drugs.

An information provider 504 includes, but is not limited to, any one or more manager(s) and/or owner(s) of a database or having access to a database containing information regarding prescriber 502, such as, but not limited to, physician verification services, credit bureaus, federal and state government regulatory agencies, professional associations, and the like. Generally, any provider of information regarding prescriber 502, and that is connected to the communication network 510, may be used.

A drug sample fulfillment vendor 506 includes, but is not limited to, entities capable of receiving drug sample order requests, filling, or having filled, the drug sample order requests, and shipping, or having shipped, the drug samples to the prescriber 502.

A drug sample fulfillment platform 508 is one or more computers or one or more programs executing on one or more computers that respond to requests of a user, such as the prescriber 502, the drug sample fulfillment vendor 506, and the information provider 504.

Figure 6A:
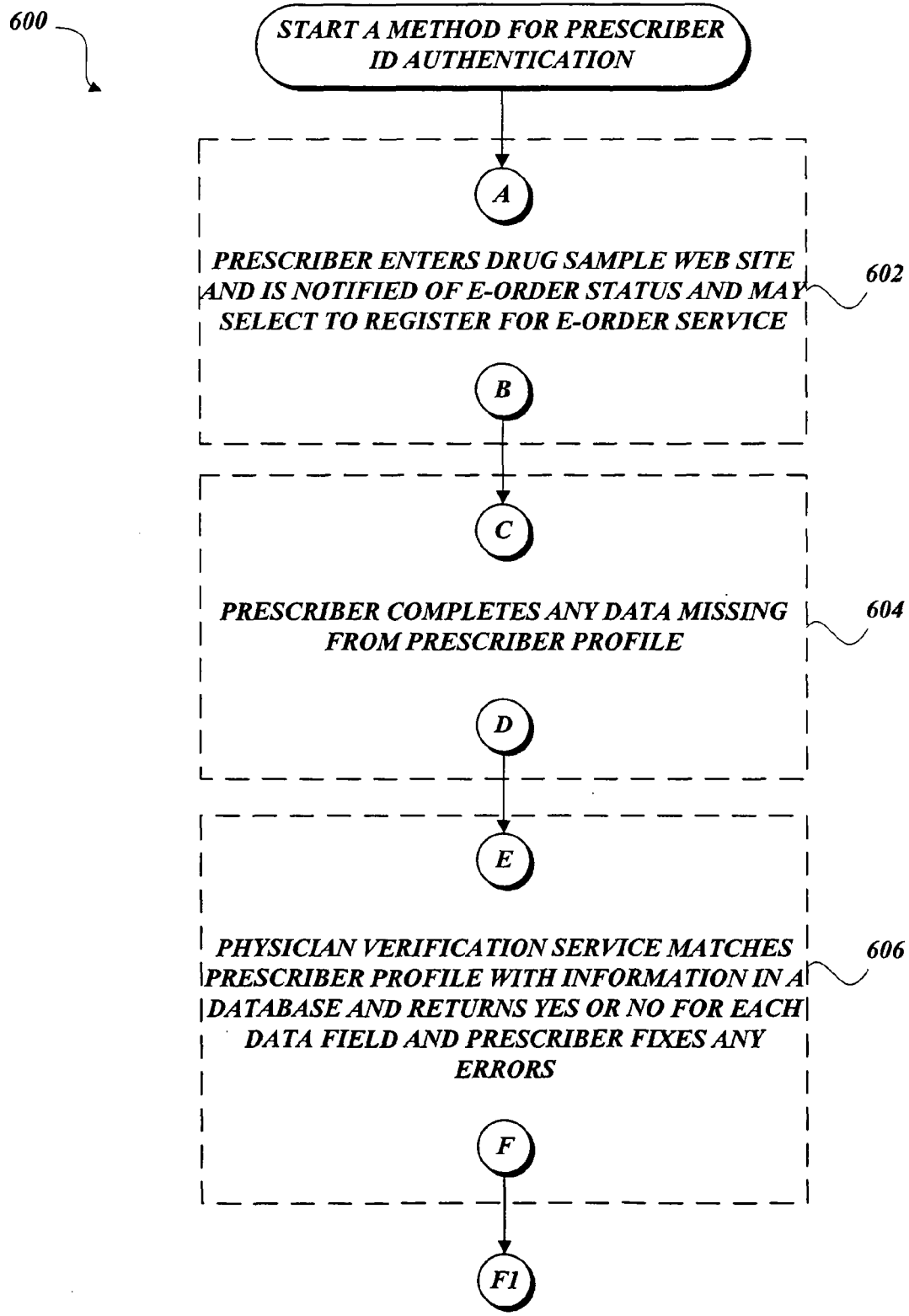
FIGS. 6A-6C are process diagrams illustrating a method for authenticating a prescriber over a communication network, according to one embodiment of the present invention.
Figure 6B:
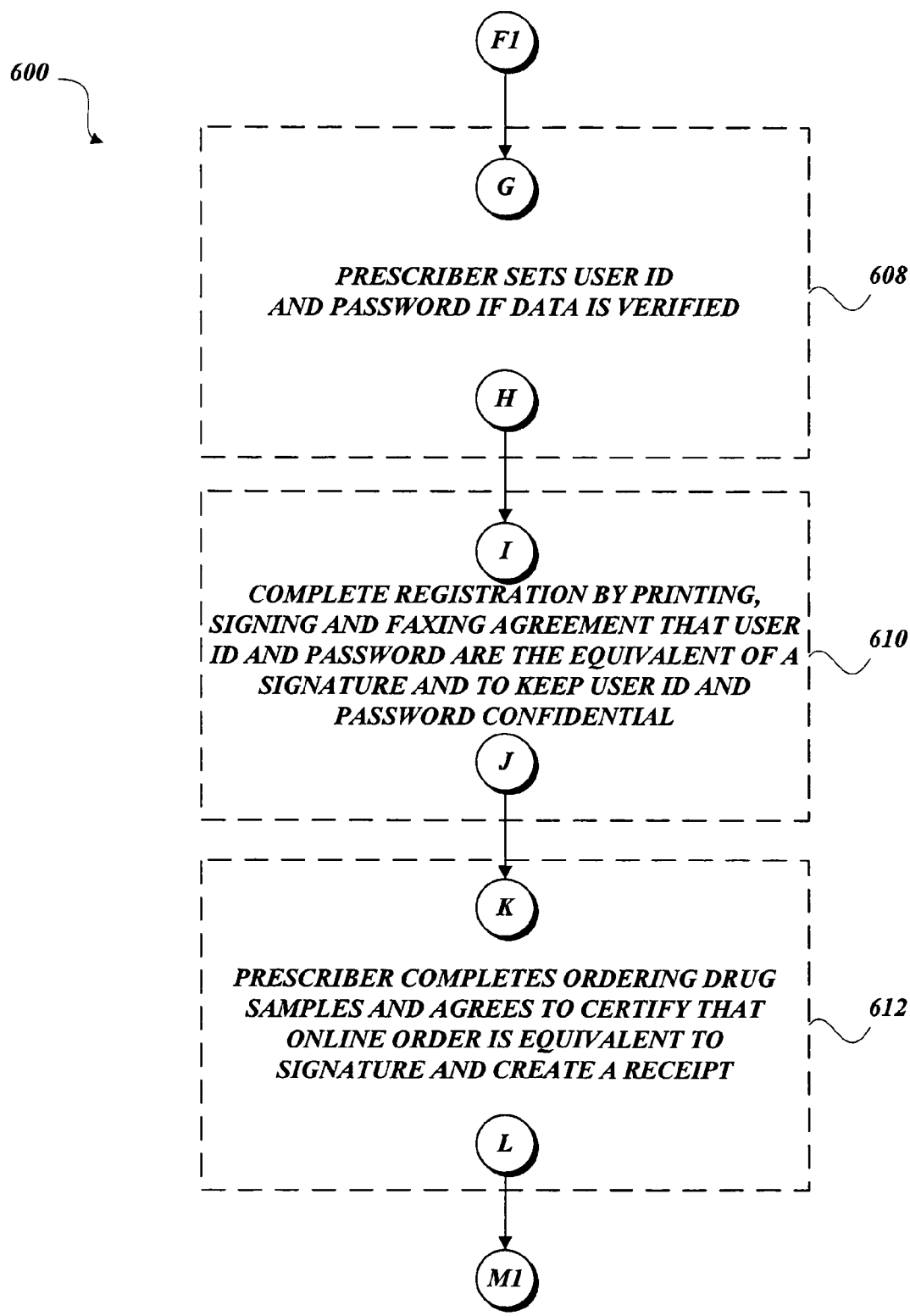
Figure 6C:
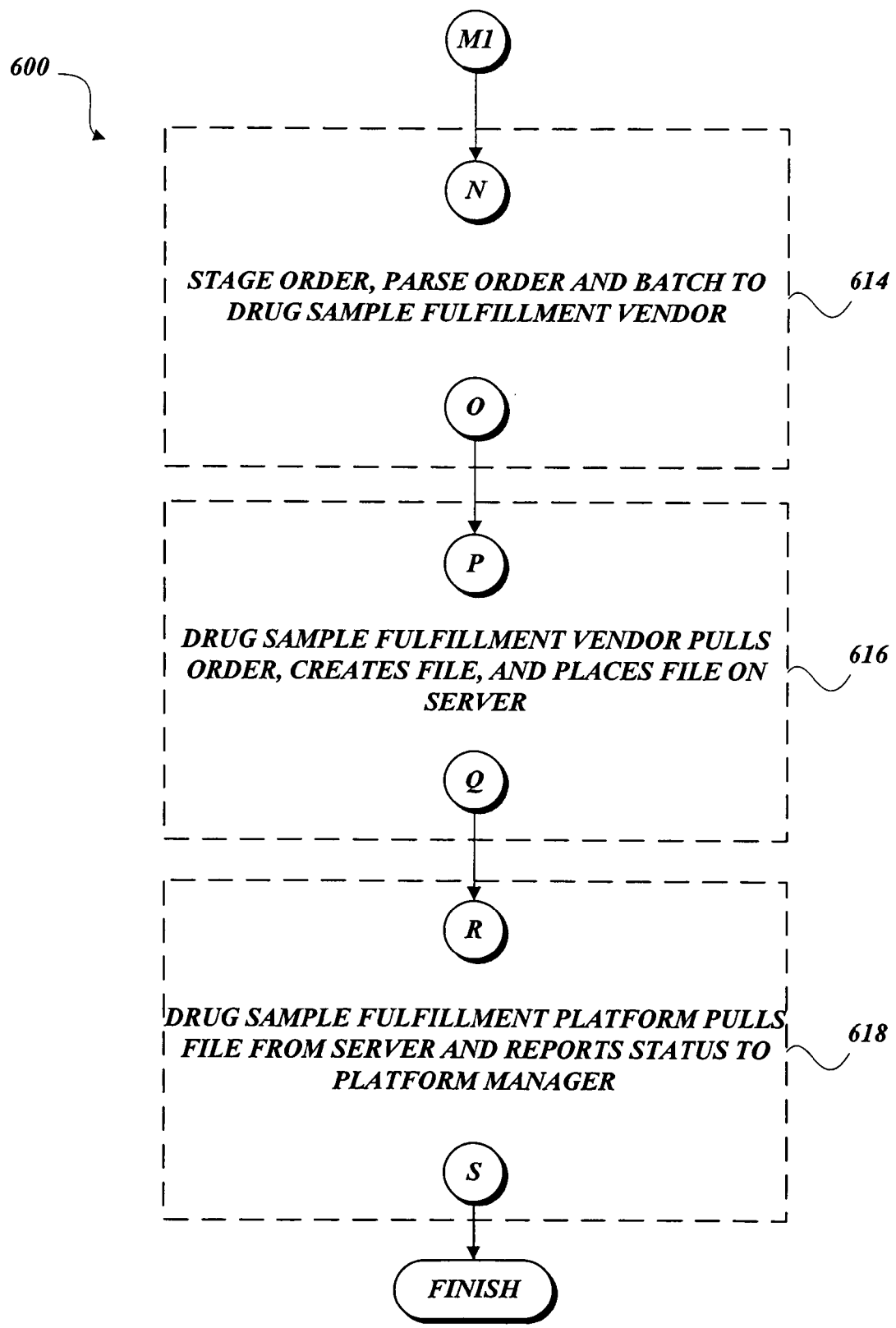

Referring now to FIGS. 6A-6C, a method 600 for ordering drug samples, including authenticating a prescriber, over a communication network, is illustrated. Reference will also be made to FIGS. 7A-7G, representing Web pages 726A-726G.

Figure 7A:
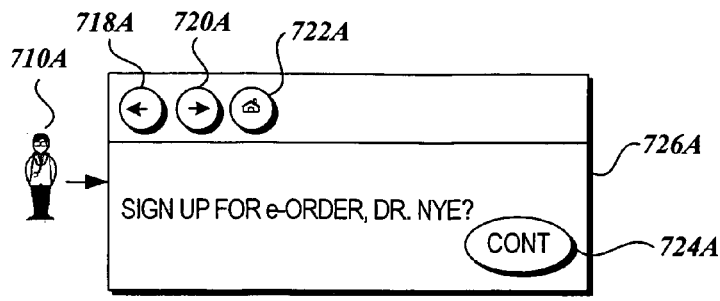
FIGS. 7A-7G are pictorial diagrams illustrating various Web pages to authenticate a prescriber over a communication network, according to one embodiment of the present invention.

Between Terminal A and Terminal B, a set of steps is defined in block 602 for a prescriber to register for a service to electronically order drug samples online (e-order). E-ordering services refers to orders that may be placed over a communication network. E-ordering services may include, but are not limited to, ordering physical drug samples over the Internet. While the present invention may be discussed in the context of ordering prescription drug samples, it is possible that other substances or products may also be ordered electronically in accordance with the invention. When the prescriber logs onto the drug sample Web site 230, the first Web page that appears may have a notice indicating whether or not the prescriber is enabled to use e ordering services. See Web page 302A (FIG. 3A). If the prescriber is not enabled, which may be represented by an "X" over an e-order icon, then the method may also include prompting the prescriber to register for e ordering services via a new Web page, such as Web page 726A (FIG. 7A).

Figure 7B:
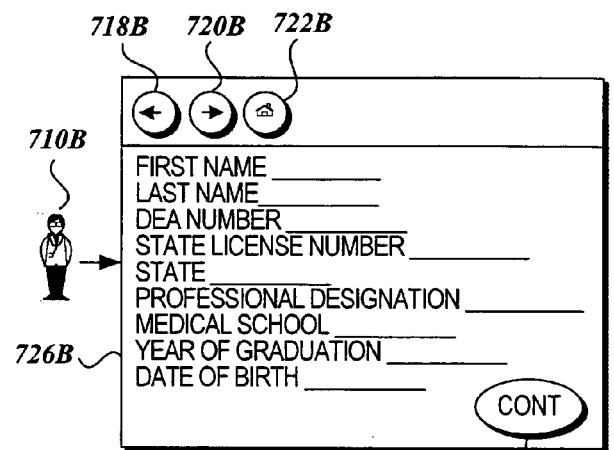

Between Terminals C and D, a set of steps is defined in block 604 for obtaining from the prescriber a prescriber profile containing various authentication descriptors. In one embodiment, the authentication descriptors include the prescriber's first name, last name, DEA number, state medical license number, state of licensure, professional designation, medical school attended, year of medical school graduation, and date of birth. Such number and type of authentication descriptors are believed to comply with the Food and Drug Administration (FDA) requirement to verify a prescriber. See Web page 726B (FIG. 7B).

Figure 7C:
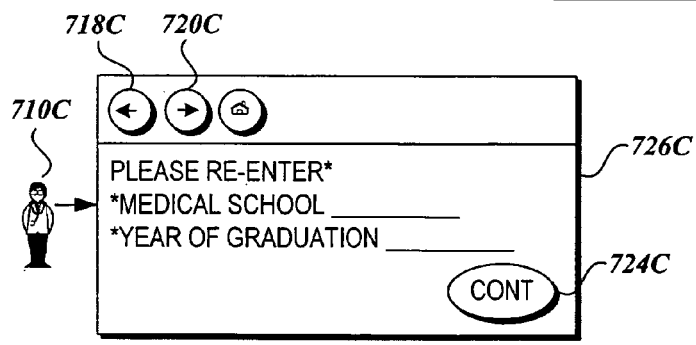

Between Terminals E and F, a set of steps is defined in block 606 for verifying the person entering the information in the subscriber profile, is in fact, the prescriber characterized by such information. By requiring authentication descriptors that only the true prescriber would know, authentication of the prescriber may be ascertained with as high a level of certainty as with a signature. The prescriber profile created in block 604 may be transmitted over a communication network, and the prescriber's authentication descriptors are compared with information from databases that have information about prescribers. Such databases generally are maintained by PVS, which receive their information from the AMA, and state licensing entities. Alternatively, other entities besides a PVS can be utilized, for example, a credit bureau, or any other state or federal government agency that may have information related to the prescriber. The PVS is preferred for their reliability. Alternatively, more than one information provider may be used. For example, if authenticating a prescriber against a credit bureau, the amount of information that needs to be provided would be greater than if authenticating against a PVS. The PVS may return a "YES" or "NO" response for each authentication descriptor, indicating whether the information matches the information in the PVS database. If there is a mismatch in any authentication descriptor, the prescriber may be given a limited number of attempts to complete the prescriber profile with accurate information. Only those authentication descriptors that were incorrect may need to be re-entered by the prescriber. See Web page 726C (FIG. 7C).

Figure 7D:
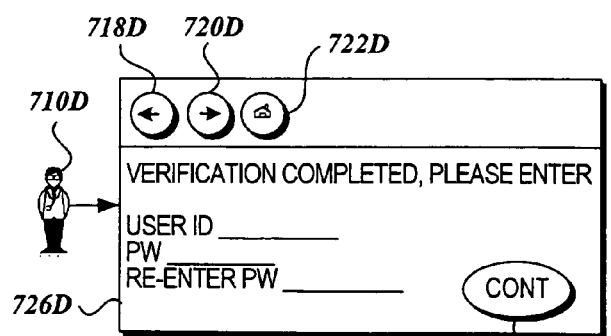

Between terminals G and H, a set of steps is defined in block 608 for the prescriber to set a password and a User ID for initially opening an account for e-ordering services. The User ID can be the state medical license number, and the password is preferably a strong password, such as a password requiring letters and numbers and having a minimum length. See Web page 726D (FIG. 7D). At a future time, if the prescriber wishes to utilize e-ordering services, the prescriber may simply order the drug samples using the established User ID and password as an electronic signature, without having to undergo the authentication process every time the prescriber wishes to order sample drugs online. However, the password may be set to expire at a predetermined time, and the prescriber may have to re-new the authentication process at such time. Such measure is to ensure that only currently authorized prescribers are kept in the system.

Figure 7E:
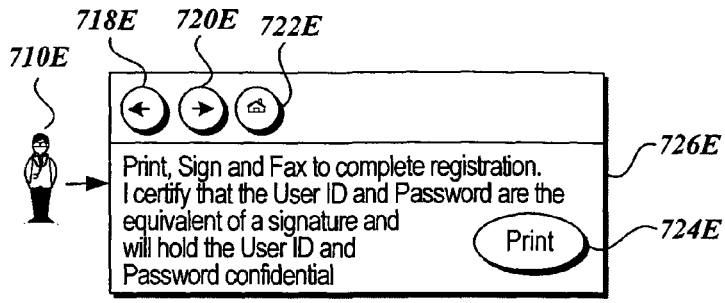

Between terminals I and J, a set of steps is defined to complete registration. The prescriber may be requested to print, sign and fax an agreement made with the drug sample fulfillment platform manager, wherein such agreement may ask the prescriber to agree to the User ID and password being the equivalent of a signature, and additionally requesting the prescriber to maintain the User ID and password in confidence. See Web page 726E (FIG. 7E). As an additional precaution against possible fraud, once a prescriber completes the registration process, the drug sample fulfillment platform manager may send a document to the prescriber to an address provided by the PVS. The document may notify the prescriber of successful registration for electronic ordering and request immediate notification if the prescriber has not requested such registration. Additionally, the document may once again request the prescriber to maintain the User ID and password confidential to prevent fraudulent use. After registering for e-ordering service, the prescriber may wish to return to the home page of the drug sample Web site to begin the selection of drug samples and complete the ordering process.

Figure 7F:
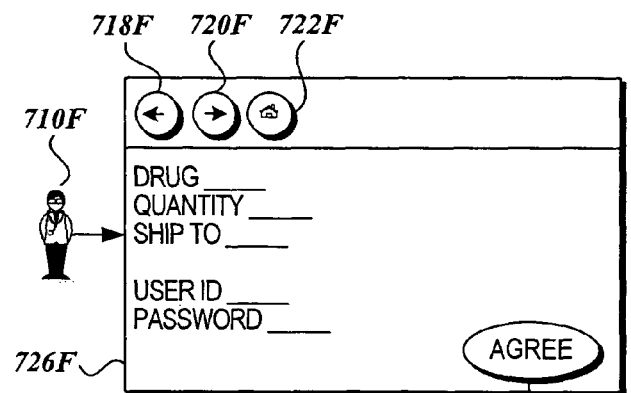
Figure 7G:
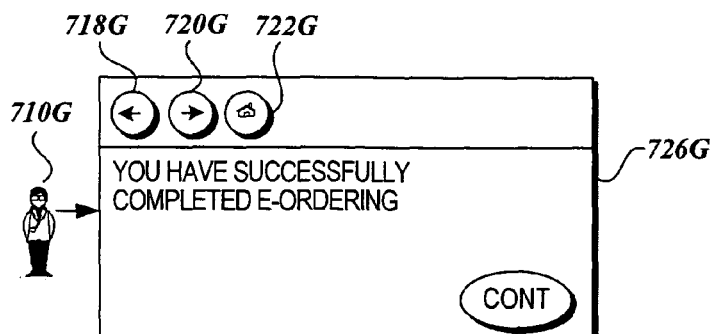

Between terminals K and L, a set of steps is defined in block 610 for the prescriber to complete the selection of the drug samples in accordance with the brand rules, discussed above. The method requires the prescriber to complete ordering drug samples and then submit the drug sample order by entering the User ID, Password, and agreeing to certify that the order to be sent electronically is the equivalent of a faxed order with a handwritten signature. See Web page 726F (FIG. 7F). A receipt may be created and maintained by the drug sample fulfillment platform manager as evidence of the prescriber's having certified the order sent electronically.

Between terminals N and O, a set of steps is defined in block 614 for staging the drug sample order, parsing the order if necessary, and batching the order at predetermined times to drug sample fulfillment vendors. It is possible that drug sample orders may contain a variety of drugs, each sold by a different vendor. Accordingly, the drug sample order has to be parsed according to vendors, and each vendor will receive an order for only the drugs that the vendor carries. The order may be stored as a file and downloaded to a server, such as an FTP (file transfer protocol) server. Preferably, the drug sample order is encrypted for secure transmission to the drug sample fulfillment vendors.

Between terminals P and Q, a set of steps is defined in block 616 for the drug sample fulfillment vendor to pull the order from the server and process the order. The fulfillment vendor decrypts the order. The fulfillment vendor processes the drug sample order, fills and ships the order to the address associated with the prescriber. The drug sample fulfillment vendor may create a file on a daily basis, and place the file on a server for downloading by the drug sample fulfillment platform. The file created by the drug sample fulfillment vendor may have the status of the order; indicating one of three possibilities, the order may have been filled and shipped, the order may have contained an error, or the order may have been rejected.

Between terminals R and S, a set of steps is provided in block 618 for the drug sample fulfillment platform to pull the file from the vendor server and report the status of the order to the drug sample fulfillment platform manager. At this point, the platform manager may record or log the status of all orders.

Referring to FIGS. 7A-7G, a series of Web pages 726A-726G, are illustrated. Web pages 726A-726G are representative of Web pages that may be used in the authentication of a prescriber to enable e ordering drug samples over a communication network. Web pages 726A-726G and associated content may be downloaded from the drug sample fulfillment platform 208. Web pages 726A-726G include generally a back browse button 718A-718G, a forward browse button 720A-720G, and a home button 722A-722G.

Web page 726A may be used to prompt a prescriber 710A to register for e-ordering drug samples. E-ordering requires the prescriber 710A to undergo an authentication procedure before being allowed to order online. Web page 726A may appear when the prescriber 710A selects the link "REGISTER FOR E-ORDER" in area 316 of Web page 302A (FIG. 3A). The Web page 726A prompts the prescriber 710A to select the CONT button 724A to continue with the registration process for e-ordering services. Otherwise, the prescriber 710A may select the HOME button 722A and return to the home Web page.

If the prescriber 710A elects to register for the e-ordering service by selecting the CONT button 724A, Web page 726B may appear next.

Web page 726B includes the form to be filled in by the prescriber to create the prescriber's 710B profile. The prescriber profile contains authentication descriptors that is information characteristic of the prescriber 710B. Such authentication descriptors are compared against the known information of the prescriber from an external, independent or government database. If every authentication descriptor in the prescriber's profile or a selected set of authentication descriptors in the prescriber's profile matches the information found in these databases, the prescriber 710B may be enabled to order drug samples online. The prescriber's profile may include, but is not limited to the prescriber's first name, last name, DEA number, state medical license number, state of licensure, professional designation, medical school attended, year of graduation, and date of birth. The detail of information that is required is likely to deter imposters. Once the prescriber 710B fills in the missing information, the prescriber 710B can select the CONT button 724B.

Upon actuation of CONT button 724B, the prescriber profile information is sent over a communication network, such as the Internet, to an information provider. The information provider may utilize one or more source of prescriber information, such as can be provided by the AMA, state licensing entities or any other source of prescriber information including, but not limited to, credit bureaus, banks, state driver's license office, and the like. An algorithm is applied that attempts to match each authentication descriptor or a selected set of authentication descriptors in the prescriber profile in Web page 726B with information residing with the information provider.

Web page 726C is an exemplary Web page that may appear if the prescriber 710C fails to provide any authentication descriptor in the prescriber profile of Web page 726B that does not match with prescriber information from the provider of prescriber information. For example, Web page 726C shows that the prescriber failed to enter the correct medical school and year of graduation for the person that was listed by first and last name in the prescriber profile in Web page 726B. The prescriber 710C may be given a maximum number of attempts to correct the information. Preferably, the prescriber 710C will have additional opportunities to correct any misspellings. After re-entering any authentication descriptor that may have been incorrect, or otherwise did not match the information of the information provider, the prescriber 710C may attempt authentication again by selecting the CONT button 724C.

Upon selecting the CONT button 724C, transmittal of the new information to the information provider, and the application of a matching algorithm, are carried out. Thereafter, a Web page, such as Web page 726D may appear. Web page 726D is an exemplary Web page that may be displayed when all of the prescriber profile information or a selected set of prescriber profile information has been matched correctly and has been verified to be accurate for the named person. Web page 726D prompts the prescriber 710D to enter a User ID and a password. Preferably, the User ID is the prescriber's state medical license number. The User ID and the password are required to enable the prescriber 710D to set up an account for ordering drug samples online. Preferably, the prescriber is authenticated at regular intervals to ensure that the system is kept current with only authorized prescribers. Because the prescriber will not be sending a signature to be matched with a signature on file, the method in accordance with the invention provides that only persons who are truly authorized to prescribe may do so, and denies access to all others. Preferably, the length of time the prescriber may use the same password is monitored, and the prescriber 710D may be limited to using any one password for not more than six months, for example. Furthermore, the password is preferably a strong password that may include both letters and numbers. The prescriber 710D can select the CONT button 724D after entering a User ID and a password.

Upon actuation of the CONT button 724D, Web page 726E may appear. Web page 726E is representative of a Web page that may be displayed after the prescriber 710E has successfully entered a User ID and a password. Web page 726E is an enrollment form to complete registration. In Web page 726E, the prescriber 710E may be requested to print, sign and fax an enrollment form provided by the drug sample fulfillment platform manager, wherein such enrollment form may ask the prescriber to agree to the User ID and password being the equivalent of a signature, and additionally requesting the prescriber to maintain the User ID and password in confidence. Preferably, registration for the e-ordering service may not be completed until the signed and faxed enrollment form is received by, and processed by, the drug sample fulfillment platform manager. However, since the prescriber 710E may immediately wish to order drug samples, the prescriber 710E may be allowed one or a limited number of trial electronic online drug sample orders, while awaiting for the enrollment form to be processed. Prescriber 710E may select the PRINT button 724E to print the agreement. Thereafter, a Web page may be called up that may be used to select sample drugs for ordering online. Alternatively, the prescriber 710E may wish to go to the home Web page by selecting the HOME button 722E, and conduct other interactions with the home Web page. At a future time, the prescriber 710E may enter a Web page, such as Web page 726F.

Web page 726F is representative of a Web page that may be used for ordering drug samples online. Web page 726F includes information such as the drug name, the quantity, and the shipping address. To complete the order and send the order over a communication network without having to sign and fax the order, the prescriber 710F is required to have access to the e-order account, which the prescriber will have created in the same session only earlier, or in a past session on the drug sample fulfillment Web site. The prescriber 710F is prompted to enter the User ID and the password recognizable for the account. The Web page 726F may include a statement giving notice to the prescriber 710F that the User Id and password used with the order to be sent to the drug sample fulfillment vendor is certified to be the equivalent of a handwritten signature.

If the prescriber 710F agrees to the conditions and terms of the e-ordering service by selecting the AGREE button 726, a Web page, such as Web page 726G, may appear. Web page 726G notifies the prescriber that the prescriber 710G has successfully completed electronically ordering drug samples online.

Figure 8:
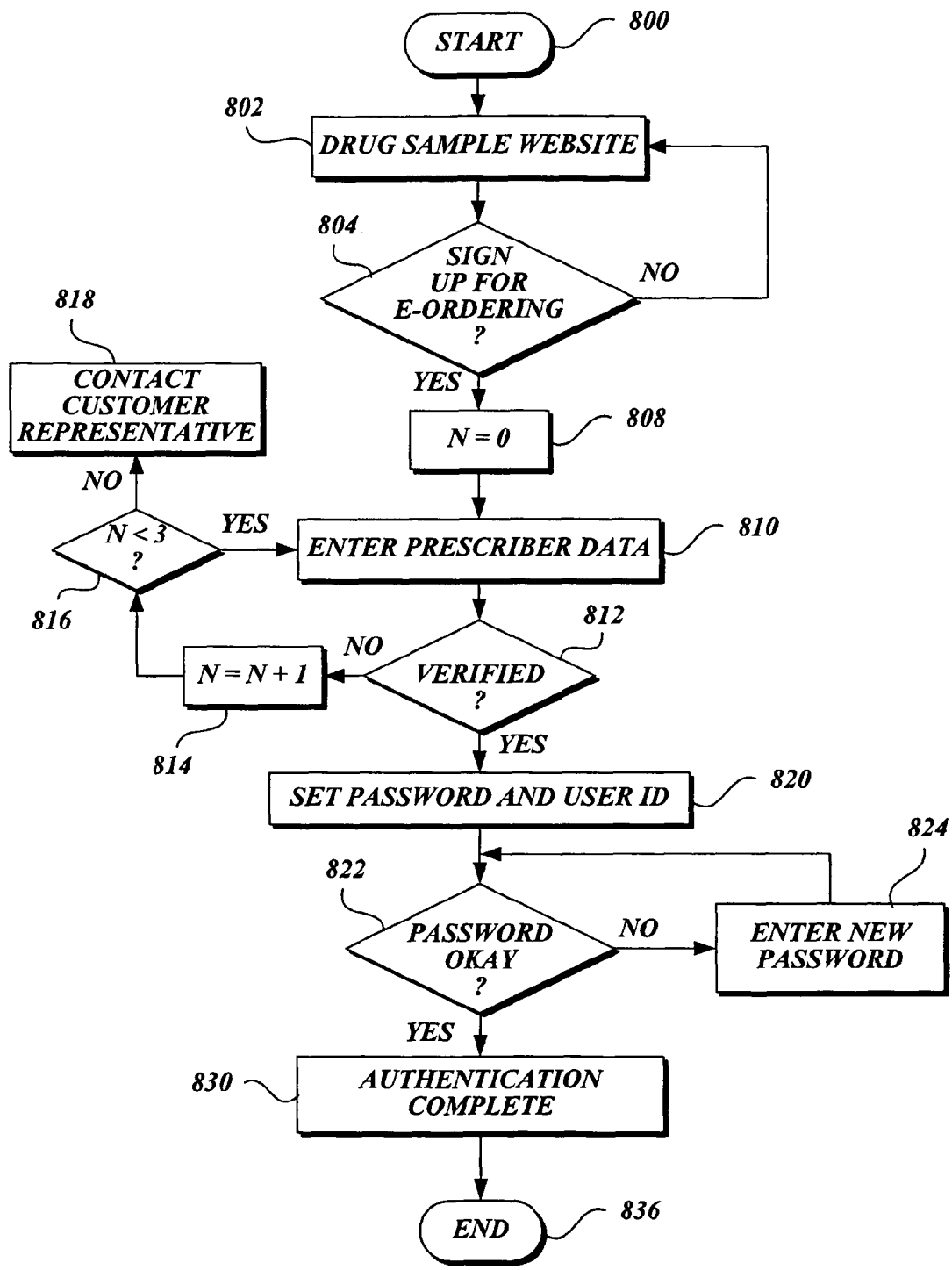
FIG. 8 is a process diagram illustrating a method for authenticating a prescriber, according to one embodiment of the present invention.

Referring now to FIG. 8, a flow diagram illustrating a method defined between starting block 800 and ending block 836, for the authentication of a prescriber to enable ordering drug samples online, over a communication network, is provided.

In block 802, the method starts with the prescriber being at the drug sample fulfillment Web site 230. See FIG. 2C. While in the drug sample fulfillment Web site 230, the prescriber may perform a variety of interactions. At least one interaction on the drug sample fulfillment Web site 230 includes the option to register for ordering online drug samples.

Block 804 is a test for determining whether the prescriber has selected to register for ordering drug samples online. As long as the prescriber does not select to register, the test of block 804 is continually checking for a "YES," otherwise the test result is "NO," and the method remains in the drug sample Web site 230.

Upon detecting a "YES" response to the test of block 804, a counter may be initialized to zero in block 808. The counter designated by the letter "N" in block 808 is for keeping track of the number of attempts made at entering valid prescriber authentication descriptors.

In block 810, the prescriber enters the prescriber authentication descriptors. The prescriber authentication descriptors entered in block 810 are transferred over a communication network to an information provider that attempts to match all or a selected set of prescriber authentication descriptors entered in block 810 with the information provider's information obtained from a variety of sources.

In block 812, a test is made to determine whether the prescriber authentication descriptors entered in block 810 match with the prescriber information that is obtained from one or more sources by the information provider. Such source for prescriber information may include the AMA, a state medical licensing entity, a credit bureau, and the like.

If the test in decision block 812 is "NO," meaning one or more authentication descriptors are not verified, the counter "N" is incremented by a value of "1" in block 814, meaning that the prescriber has used up one attempt at entering valid prescriber authentication descriptors.

At block 816, a test is made to determine whether the prescriber has used up all the available attempts at entering valid prescriber authentication descriptors by comparing the current number of attempts with the maximum number of permitted attempts. In this example, the maximum number of attempts is three. As long as the actual number of attempts remains less than the maximum, then, the prescriber may continue to attempt entering authentication descriptors to correct those that were incorrectly entered. If the test at decision block 816 is "NO," meaning that the prescriber has used up all the attempts at entering valid prescriber authentication descriptors, the prescriber may be directed to contact a customer representative for assistance in block 818. If the test at decision block 816 is "YES," meaning that the prescriber has remaining attempts at entering valid prescriber authentication descriptors, the prescriber is given the opportunity to once again enter prescriber authentication descriptors in block 810. The newly re-entered authentication descriptors are again transmitted over a communication network to the information provider that attempts to match the prescriber-entered authentication descriptors with the information provider's information.

If the answer to the test in block 812 is finally "YES," meaning that the authentication descriptors provided by the prescriber match those of the information provider's, the prescriber is allowed to set a password and a User ID in block 820 to open an account for ordering drug samples online. A User ID and password is required so that preferably no one but the authenticated prescriber can order drug samples online. Preferably too, the prescriber should not be required to be authenticated each and every time the prescriber orders drug samples online.

In block 822, a test is made to determine whether the password that was entered by the prescriber in block 820 is acceptable. The password test can be any of a number of tests. For example, any of the following password tests may be used: the password must have a certain minimum number of characters, the password must include at least one numeral, or the password cannot be reused more than once, etc. If the password entered by the prescriber in block 820 passes the test in block 822, the authentication and the opening of an online ordering account is considered to be completed in block 830.

If the password entered by the prescriber in block 820 does not pass the test in block 822, the prescriber is prompted to enter a new password in block 824. The prescriber is repetitively prompted to enter a new password until the prescriber enters a valid password and passes the test in block 822. In one embodiment, if the password is allowed to expire, the prescriber must undergo a renewed authentication procedure starting at block 808. This provides greater assurance that the password is used only by authenticated prescribers.

The use of the present invention significantly improves the time from which a drug sample order is submitted to the time the drug samples are received by the prescriber. The work previously required to be performed by the prescriber, such as printing the order, signing, and then faxing the order to the drug sample fulfillment vendor is obviated by the present invention. An added benefit is the improved auditing and tracking of drug sample orders.

It should be readily understood that the use of the PVS to provide prescriber information is merely to illustrate one embodiment of the invention, and should not be construed as limiting the invention. The use of the PVS as the information provider is preferred because the service is unique to physicians and the information contained in the PVS is not generally available to the public. However, the method in accordance with the invention may be expanded to include other sources of prescriber information, including, but not limited to credit bureaus, professional associations, federal and state governmental agencies, and the like, provided that any entity may offer an interface to the prescriber information, preferably via a communication network connected to the drug sample fulfillment platform. Furthermore, the use of the particular authentication descriptors in the prescriber profile is again merely to illustrate one embodiment of the invention and should not be construed as limiting of the invention. In the case of credit bureaus, for example, the prescriber profile may have authentication descriptors that include mortgage dates, for example. If the information provider is a driver's license office, the prescriber profile may have authentication descriptors that include a driver's license number, for example.

In another embodiment of the invention, the prescriber may be offered the choice of authenticating against either a credit bureau, or a state agency database, or both. Authentication is deemed complete when the prescriber has successfully authenticated to as many databases as the situation requires. This embodiment is useful when many databases are available, but are of low stability or reliability.

In yet another embodiment of the invention, the prescriber may have the option of deciding which authentication descriptors of the prescriber profile to complete. Authentication descriptors may be designated as "required" or "optional," or alternatively, some authentication descriptors may even be assigned a weight. For example, strongly identifiable authentication descriptors, such as the first/last name combination may be assigned a high weight, while easily obtained information, such as an automobile license plate may be assigned a relatively low weight. Provided that the prescriber-entered authentication descriptors are correct, a weighted value can be obtained. The threshold value for considering when authentication is confirmed is set sufficiently high so that authentication may only be achieved by correctly entering the higher weighted authentication descriptors plus some of the lower weighted authentication descriptors. The prescriber then has the choice of which low-weight authentication descriptors to use and can use information that is easily remembered by the prescriber or for which the prescriber has fewer concerns about privacy.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for authenticating a prescriber over a communication network for placing an order for a drug, the method comprising:
    obtaining, by an authentication computing device, prescriber authentication descriptors that are characteristic of the prescriber, wherein the number of the prescriber authentication descriptors obtained is based on the reliability of a provider of prescriber information as a source of prescriber information;
    verifying, by the authentication computing device, a match of the prescriber authentication descriptors with the prescriber information received from the provider of prescriber information; and
    enabling, by the authentication computing device, the prescriber to order the drug over the communication network when a selected set of prescriber authentication descriptors match with the prescriber information received from the at least one provider of prescriber information.

2. The method of claim 1, wherein the provider of prescriber information is a physician verification service, a credit bureau, a state agency, a federal governmental agency, a professional association, or any combination thereof.

3. The method of claim 1, wherein the drug is a prescription drug sample.

4. The method of claim 1, further comprising selecting the drug to order and placing an order for the drug without requiring a handwritten signature.

5. The method of claim 1, wherein the prescriber authentication descriptors include at least one of a prescriber's first name, a prescriber's last name, a drug enforcement agency number, a state medical license number, a state of licensure, a professional designation, a medical school, a year of graduation from a medical school, and a date of birth.

6. The method of claim 1, further comprising opening an online drug sample ordering account.

7. The method of claim 1, further comprising setting a user ID and password to enable an online drug sample ordering account.

8. The method of claim 1, further comprising indicating prescriber authentication descriptors that do not match and allowing the prescriber to correct any prescriber authentication descriptors that do not match.

9. The method of claim 1, further comprising allowing the prescriber to correct any of the prescriber authentication descriptors that do not match and placing a limit on a number of attempts to correct the prescriber authentication descriptors that do not match.

10. The method of claim 1, further comprising matching the prescriber authentication descriptors with information provided from more than one information provider.

11. The method of claim 1, wherein some of the prescriber authentication descriptors are optional and some of the prescriber authentication descriptors are required.

12. A networked system for authenticating the identity of a prescriber of pharmaceutical drugs, comprising:
    a computing device including a memory and a processor; and
    a drug sample fulfillment platform comprising executable instructions stored on the memory which, when executed by the processor, cause a drug sample Web site to mate with a Web portal when a prescriber selects a hyperlink, the drug sample Web site presenting one or more Web pages for authenticating an identity of the prescriber when received prescriber authentication descriptors match with received prescriber information such that a threshold of points associated with the prescriber authentication descriptors is reached, wherein the drug sample fulfillment platform is communicatively coupled via a communication network to a provider of prescriber information, and wherein the prescriber authentication descriptors are weighted.

13. The networked system of claim 12, wherein the communication network is the Internet.

14. The networked system of claim 12, wherein the provider of prescriber information is a physician verification service.

15. The networked system of claim 14, wherein the physician verification service includes prescriber information from a professional organization and a state medical licensing board.

16. A drug sample fulfillment system, comprising:
    a display configured to display a drug sample Web site for mating with a portal; and
    a request database for receiving requests of a prescriber through the drug sample Web site for drug samples, the request database responding to the prescriber by allowing the prescriber to place an order for drug samples after the prescriber has been authenticated by comparing received and weighted prescriber authentication descriptors with received prescriber information so that a threshold number of points associated with the received and weighted prescriber authentication descriptors is reached, and electronically transmitting a drug sample request order to a drug sample fulfillment vendor over a communication network.

17. The drug sample fulfillment platform of claim 16, wherein prior to transmitting the drug sample request order, the prescriber may be authenticated over the communication network by supplying a set of prescriber authentication descriptors.

18. A drug sample ordering system, comprising:
a computing device including a memory and a processor; and
a drug sample fulfillment platform comprising executable instructions stored in the memory which, when executed by the processor, cause a prescriber authentication engine to authenticate the identity of a prescriber by comparing a plurality of weighted authentication descriptors characteristic of the prescriber against prescriber information from an information provider of prescriber information so as to reach a threshold number of points associated with the plurality of weighted authentication descriptors, and obtaining a confirmation for each of the weighted authentication descriptors that match with the prescriber information, wherein, when authenticated, the prescriber may order drug samples via the drug sample fulfillment platform.

19. The drug sample ordering system of claim 18, wherein ordering of drug samples takes place electronically over a communication system.

20. A method for processing a drug sample request order received over a communication network, the method comprising;
obtaining, by an authentication computing device over the communication network, the drug sample request order, wherein the drug sample request order is from a prescriber that may be authenticated by comparing weighted prescriber provided information against prescriber information obtained from a provider of prescriber information, wherein the weighted prescriber information includes authentication descriptors each being associated with a point value; and
processing, by the authentication computing device, the drug sample request order.

21. The method of claim 20, wherein the drug sample request order does not include a handwritten signature.

22. The method of claim 20, wherein the prescriber is authenticated when a comparison of the weighted prescriber provided information against prescriber information obtained from the provider of prescriber information reaches a predetermined threshold through an aggregation of each point value associated with the authentication descriptors that match the prescriber information.

* * * * *